(12) United States Patent
Pfirrmann et al.

(10) Patent No.: US 11,999,709 B2
(45) Date of Patent: *Jun. 4, 2024

(54) PROCESSES FOR PREPARING OXATHIAZIN-LIKE COMPOUNDS

(71) Applicant: GEISTLICH PHARMA AG, Wolhusen (CH)

(72) Inventors: Rolf W. Pfirrmann, Weggis (CH); Hanns Moehler, Maennedorf (CH); Thomas Mueller, Wolhusen (CH)

(73) Assignee: GEISTLICH PHARMA AG, Wolhusen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/151,569

(22) Filed: Jan. 9, 2023

(65) Prior Publication Data

US 2023/0159477 A1 May 25, 2023

Related U.S. Application Data

(60) Continuation of application No. 17/150,359, filed on Jan. 15, 2021, now Pat. No. 11,591,302, which is a continuation-in-part of application No. 16/538,344, filed on Aug. 12, 2019, now Pat. No. 10,968,190, which is a division of application No. 15/535,266, filed as application No. PCT/IB2015/059741 on Dec. 17, 2015, now Pat. No. 10,392,355.

(60) Provisional application No. 62/094,580, filed on Dec. 19, 2014.

(51) Int. Cl.
*C07D 291/06* (2006.01)
*A61P 35/00* (2006.01)
*C07D 419/06* (2006.01)

(52) U.S. Cl.
CPC ............ *C07D 291/06* (2013.01); *A61P 35/00* (2018.01); *C07D 419/06* (2013.01)

(58) Field of Classification Search
CPC ...... C07D 291/06; C07D 419/06; A61P 35/00
USPC .................................................... 514/222.5
See application file for complete search history.

(56) References Cited

U.S. PATENT DOCUMENTS

| 4,829,079 | A | 5/1989 | Toja et al. |
| 9,241,943 | B2 | 1/2016 | Pfirrmann |
| 9,624,187 | B2 | 4/2017 | Pfirrmann |
| 9,844,555 | B2 | 12/2017 | Pfirrmann |
| 10,392,355 | B2 * | 8/2019 | Pfirrmann ............ C07D 419/06 |
| 10,736,902 | B2 | 8/2020 | Pfirrmann |
| 10,968,190 | B2 * | 4/2021 | Pfirrmann ............ C07D 291/06 |
| 11,591,302 | B2 * | 2/2023 | Pfirrmann ............... A61P 35/00 |
| 2008/0039506 | A1 | 2/2008 | Hattori et al. |

FOREIGN PATENT DOCUMENTS

| JP | 2010-536754 A | 12/2010 |
| WO | 2006/033446 A1 | 3/2006 |
| WO | 2009/023232 A1 | 2/2009 |
| WO | 2012024083 A1 | 2/2012 |
| WO | 2013190355 A1 | 12/2013 |

OTHER PUBLICATIONS

International Search Report cited in PCT/IB2015/059741 dated Feb. 24, 2016, 6 pages.
English language translation First Office Action cited in Chinese Application No. 201580072835.0 dated May 23, 2018, 14 pages.
Office Action issued for European patent Application No. 15821172.2 dated Oct. 18, 2018, 7 pages.
Office Action issued for Indian Patent Application No. 201737024698 dated Oct. 24, 2019, 6 pages.
Office Action issued for Brazilian Patent Application No. BR112017013188-9 dated Sep. 15, 2020, 8 pages.
Office Action issued in the corresponding Chinese Patent Application No. 2019109743144 dated Aug. 17, 2022 with English translation, 16 pages.
Oda, Ryohei et al., "Research upon Joint Reaction and Transjointing. (III)," Bulletin of the Institute for Chemical Research, Kyoto University 1955, vol. 33, No. 4, pp. 117-125.
Lee et al., Practical Synthesis of Sultams via Sulfonamide Dianion Alkylation: Application to the Synthesis of Chiral Sultams, Organic Letters, 2003, vol. 5, No. 22, pp. 4175-4177.

\* cited by examiner

*Primary Examiner* — Kahsay Habte
(74) *Attorney, Agent, or Firm* — ROTHWELL, FIGG, ERNST & MANBECK, P.C.

(57) ABSTRACT

Oxathiazin-like compounds, processes for making new oxathiazin-like compounds, compounds useful for making oxathiazin-like compounds, and their uses are disclosed. Processes of treating patients suffering from cancers, bacterial infections, fungal infections and/or viral infections by administering oxathiazin-like compounds are also disclosed. These compounds were found to have significantly longer half-life compared to taurolidine and taurultam.

20 Claims, 15 Drawing Sheets

PROCESSES FOR PREPARING OXATHIAZIN-LIKE COMPOUNDS

CROSS-REFERENCE TO RELATED APPLICATIONS

The present application is a continuation of U.S. application Ser. No. 17/150,359 filed on Jan. 15, 2021, which is a continuation-in-part of U.S. application Ser. No. 16/538,344, filed on Aug. 12, 2019, and granted as U.S. Pat. No. 10,968,190, which is a division of U.S. application Ser. No. 15/535,266, filed on Jun. 12, 2017, and granted as U.S. Pat. No. 10,392,355, which is a National Stage Entry of PCT/IBS2015/059741, filed on Dec. 17, 2015, which claims priority benefit of U.S. provisional Appl. No. 62/094,580, filed on Dec. 19, 2014, the disclosures of which are incorporated herein by reference in their entireties.

BACKGROUND OF THE INVENTION

Field of the Invention

The present invention relates to new compounds, processes for preparing new compounds and uses thereof.

Description of the Background Art

Oxathiazin-like compounds are known from U.S. Pat. Nos. 3,202,657 and 3,394,109.

There remains a need in the art for new compounds and processes for making such compounds to provide compounds with more potent antineoplastic and antimicrobial activity, less toxicity and side effects, and less resistance to treatment by tumor or microbial cells.

Cutaneous squamous cell carcinoma (cSCC) represents a major problem in dermato-oncology because it can be a life-threatening disease and effective and safe treatments are very limited. There remains a significant unmet need for suitable therapeutic options for treating squamous cell carcinomas.

Tumor-related morbidity and mortality are often due to migration or metastasis of the original tumor cells to a site away from the original primary tumor. Inhibition of tumor and cancer cell migration is a long-felt and unmet need in improving the prognosis of patients with tumors. There remains a significant unmet need for suitable therapeutic options for preventing, inhibiting and reducing tumor and cancer cell migration and metastases.

SUMMARY OF THE INVENTION

In accordance with the present invention, new oxathiazin-like compounds, processes for making new oxathiazin-like compounds, compounds useful for making oxathiazin-like compounds, and their uses are disclosed.

In one aspect, the present disclosure provides a method of reducing or inhibiting cancer cell migration in a subject in need thereof comprising administering an effective amount of a compound of the present disclosure to the subject. In some aspects, the compound may be a compound of formula I:

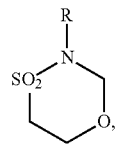
Formula I wherein R is H, an alkyl, or benzyl.
In one aspect, the compound is

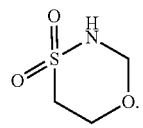
2250

In one aspect, the subject has a tumor, cancerous cells, pre-cancerous cells, or cancer stem cells, is suspected of having a tumor, cancerous cells, pre-cancerous cells, or cancer stem cells, or is at risk of developing a tumor, cancerous cells, pre-cancerous cells, cancer stem cells or metastases thereof.

In one aspect, the present disclosure provides a method of treating a subject having a squamous cell carcinoma comprising administering an effective amount of a compound of the present disclosure to the subject. In some aspects, the compound may be a compound of formula I:

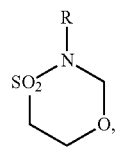
Formula I wherein R is H, an alkyl, or benzyl.
In one aspect, the squamous cell carcinoma is a cutaneous squamous cell carcinoma. In one aspect, the compound is administered orally, intravenously, topically, or a combination thereof. In one aspect, the compound is

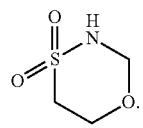
2250

BRIEF DESCRIPTION OF THE DRAWINGS

FIG. 12A shows the effects when SCC13 cells were incubated with GP-2250 (100, 150, 200, 300 and 400 µmol/l) for 24 h. FIG. 12B shows the effects when A431 cells were incubated with GP-2250 (50, 100, 125, 150 and 200 µmol/l) for 24 h. Values are expressed as mean value±SD of 8 independent experiments. Asterisk symbols indicate differences between controls. The significance levels are graphically shown as follows: *$p \leq 0.001$, $p \leq 0.01$, *$p \leq 0.05$, ns $p \leq 0.05$ (one-way ANOVA followed by Tukey's post-hoc test).

FIG. 13A shows the effects when SCC13 cells were incubated with GP-2250 (100, 150, 200, 300 and 400 µmol/l) for 6 h. FIG. 13B shows the effects when A431 cells were incubated with GP-2250 (50, 100, 125, 150 and 200 µmol/l) for 6 h. Values are expressed as mean value±SD of 3 independent experiments. Asterisk symbols indicate differences between controls. The significance levels are graphically shown as follows: *$p \leq 0.001$, $p \leq 0.01$, *$p \leq 0.05$, ns $p \leq 0.05$ (one-way ANOVA followed by Tukey's post-hoc test).

FIG. 15A shows representative images of the SCC13 cells treated with GP-2250 or negative control at 0 h, 6 h, 12 h and 24 h after the scratches were made (×10 magnification) and FIG. 15B shows the related percentage of total gap closure at 0 h, 12 h and 24 h. FIG. 15C shows representative images of the A431 cells transfected with GP-2250 or negative control at 0 h, 6 h, 12 h and 24 h after the scratches were made at the same starting point (×10 magnification) and FIG. 15D shows the related percentage of total gap closure at 0 h, 12 h and 24 h.

DETAILED DESCRIPTION OF THE INVENTION

Figure 1:
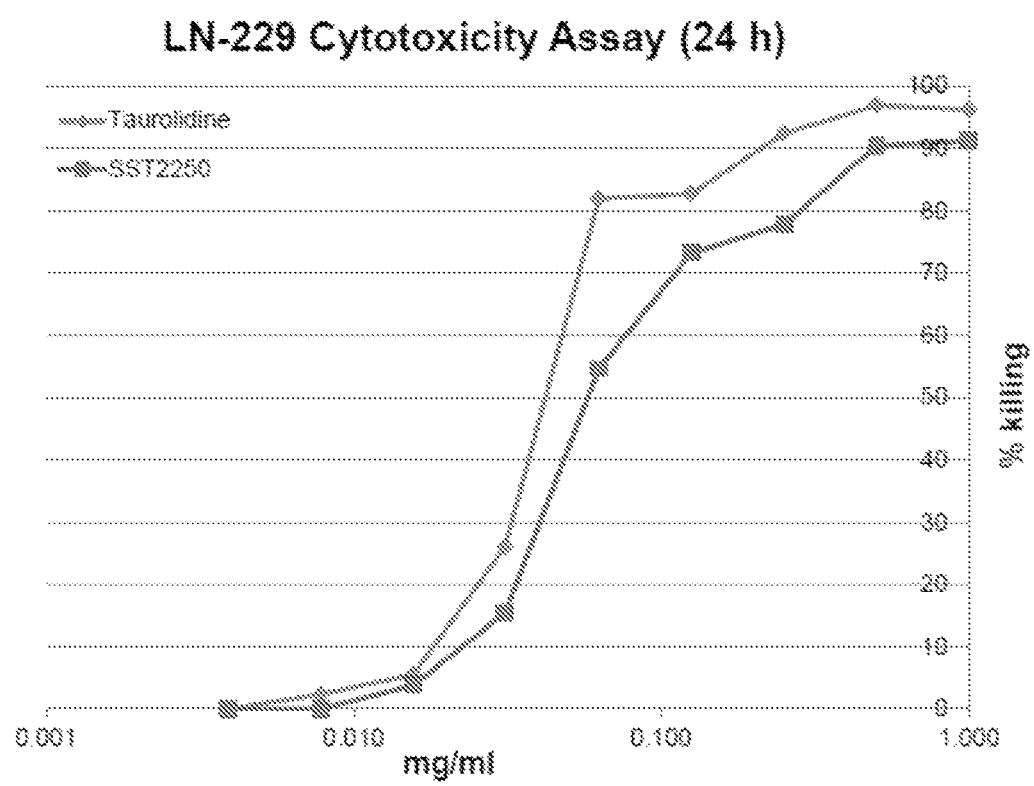
FIG. 1 graphically shows anti-neoplastic activity of one embodiment of the invention in a cytotoxicity assay in LN-229 cells.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilizing (i.e. not worsening) the state of disease, delaying or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. In addition to being useful as methods of treatment, the methods described herein may be useful for the prevention or prophylaxis of disease.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0" should be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described. Additionally, it is noted that all percentages are in weight, unless specified otherwise.

In understanding the scope of the present disclosure, the terms "including" or "comprising" and their derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of," as used herein, is intended to specify the presence of the stated features, elements, components, groups, integers, and/or steps as well as those that do not materially affect the basic and novel characteristic(s) of features, elements, components, groups, integers, and/or steps. It is understood that reference to any one of these transition terms (i.e. "comprising," "consisting," or "consisting essentially") provides direct support for replacement to any of the other transition term not specifically used. For example, amending a term from "comprising" to "consisting essentially of" would find direct support due to this definition.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. For example, in one aspect, the degree of flexibility can be within about ±10% of the numerical value. In another aspect, the degree of flexibility can be within about ±5% of the numerical value. In a further aspect, the degree of flexibility can be within about ±2%, ±1%, or ±0.05%, of the numerical value. Numerical quantities given are approximate, meaning that the term "around," "about" or "approximately" can be inferred if not expressly stated.

As used herein, the term "pharmaceutically acceptable" refers to solvents, co-solvents, surfactants, carriers, diluents, excipients, buffers, salts, and/or other components that are compatible with the other ingredients of the formulation and are not deleterious to the recipient thereof.

According to certain embodiments, the present invention relates to oxathiazin-like compounds, as well as derivatives thereof and processes and compounds for preparing oxathiazin-like compounds and derivatives thereof.

Oxathiazin-like compounds and derivatives thereof according to certain embodiments of the present invention have antineoplastic activities, antimicrobial activities and/or other activities.

Processes for making oxathiazin-like compounds and derivatives thereof according to certain embodiments of this invention provide advantageous methods for making compounds having antineoplastic activities, antimicrobial activities and/or other activities. In certain embodiments, oxathiazin-like compounds and derivatives thereof are useful, inter alia, in the treatment of cancers and tumors in a subject, such as a human patient. Accordingly, in certain embodiments the present invention also relates to treatment of cancers and tumors using compounds described herein. Cancers such as central nervous system cancers including glioblastoma, glioma, neuroblastoma, astrocytoma, and carcinomatous meningitis, colon cancer, rectal cancer and colo-rectal cancer, ovarian cancer, breast cancer, prostate cancer, lung cancer, mesothelioma, melanoma, renal cancer, liver cancer, pancreatic cancer, gastric cancer, esophageal cancer, urinary bladder cancer, cervical cancer, cardiac cancer, gall bladder cancer, skin cancer, bone cancer, cancers of the head and neck, leukemia, lymphoma, lymphosarcoma, adenocarcinoma, fibrosarcoma, and metastases thereof, for example, are diseases contemplated for treatment according to certain embodiments of the invention. Drug resistant tumors, for example a multiple drug resistant (MDR) tumor, also are useful in certain embodiments using the inventive compounds, including drug resistant tumors which are solid tumors, non-solid tumors and lymphomas. It is presently believed that any neoplastic cell can be treated using the methods described herein.

Tumor stem cells (also referred to as cancer stem cells (CSCs)) are considered to be the main drivers for the formation of metastases and the regrowth of tumors after resection.

In certain embodiments, compounds of the present invention are useful, inter alia, in the treatment of tumor stem cells in a subject.

In certain embodiments, compounds of the present invention are useful, inter alia, in the treatment of glioblastoma tumor stem cells in a subject.

In certain embodiments, the invention kills tumor cells and/or CSCs, or inhibits their growth, by oxidative stress, apoptosis and/or inhibiting growth of new blood vessels at the tumor site (anti-angiogenesis and anti-tubulogenesis). A primary mechanism of action for killing tumor cells and/or CSCs is oxidative stress. Tumor cells and/or CSCs may also be killed by apoptosis according to the invention. At lower blood concentrations, compounds according to the invention are effective at inhibiting tumor cell growth by their anti-angiogenic action and their anti-tubulogenic action, and these compounds are thus useful for palliative treatment.

Oxathiazin-like compounds and derivatives thereof of the invention metabolize much slower in the bloodstream than taurolidine and taurultam. Accordingly, lower doses of such compounds can be administered to a patient to achieve similar effects.

It was unexpectedly found that within minutes of exposure to taurolidine, tumor cells react by initiating the program of apoptotic cell death as follows:

1. The primary insult of Taurolidine to the tumor cell is an increase of reactive oxygen species (ROS), which is measured fluorimetrically.
2. The induction of oxidative stress by Taurolidine as the primary step is supported by the finding that the antineoplastic action of Taurolidine can be prevented by the addition of a reducing agent such as glutathione or N-acetylcysteine.
3. The damage caused by the elevated ROS to the mitochondria of the tumor cell results in the loss of their membrane potential and the release of Apoptosis Inducing Factor (AIF).
4. AIF is translocated to the nucleus and initiates the expression of pro-apoptotic genes, which results in the blebbing of the plasma membrane, in chromatin condensation and DNA fragmentation, the hallmarks of apoptosis.
5. In contrast to normal cells, tumor cells are very sensitive to oxidative stress. This explains the action of Taurolidine against a broad range of tumor cells, sparing normal cells.

Compounds of the present invention also are useful, in certain embodiments, in treatment of microbial infections in a subject, such as a human patient. Microbial infections which may be treated according certain embodiments include bacterial infections, fungal infections and/or viral infections.

Cancer patients tend to be immunocompromised, making them particularly susceptible to microbial infections, especially during and/or after surgery.

In certain embodiments, compounds of the invention are utilized to treat glioblastoma in a subject.

In certain embodiments, compounds of the invention are utilized to treat *S. aureus* infection in a subject.

In certain embodiments, compounds of the invention are utilized according to the invention to treat MRSA in a subject.

In certain embodiments, compounds of the invention are utilized according to the invention to treat *E. coli* in a subject.

In certain embodiments, compounds of the invention are utilized according to the invention to treat *H. pylori* in a subject, and/or cancer(s) associated with *H. pylori* in a subject.

In certain embodiments, compounds of the invention are utilized according to the invention to treat HIV in a subject.

In certain embodiments, compounds according to formula I are utilized according to the invention wherein R is H, alkyl, or the like, such as methyl, ethyl, propyl, (e.g., isopropyl), benzyl or the like.

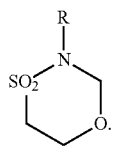

Formula I

Figure 8:
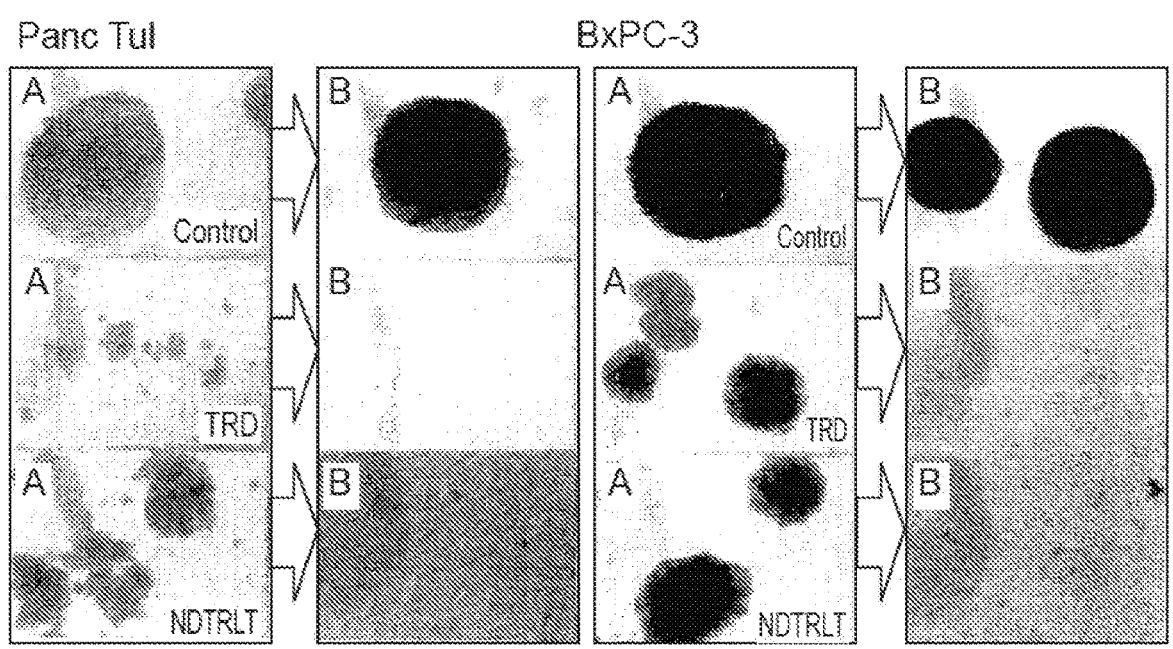
FIG. 8 shows the results of a spheroid toxicity assay for multicellular pancreatic tumor (Panc Tul or BxPC-3) spheroids in which control, taurolidine-treated (500 µM) or compound 2250-treated (1000 µM) samples were treated for 48 hours (columns labeled A) and strained to test residual aggregates (columns labeled B) for stability.

In certain embodiments, new compound 2250 (Tetrahydro1,4,5-oxathiazin-4-dioxide or 1,4,5-oxathiazan-4-dioxide) is prepared and/or utilized according to the invention. An FTIR spectrum for compound 2250 made according to the present invention is shown in FIG. 8.

In certain embodiments, new compound 2245 is prepared and/or utilized according to the invention.

Compound 2250 prevents and treats stomach tumors, including tumors caused by or associated with *H. pylori*, or tumors as a consequence of metastasis to the stomach.

The amount of the compounds needed depends on tumor size. In one embodiment, the invention includes surgically reducing tumor size and treating with one or more of the compounds. The compound may be administered before, during or after surgery to reduce tumors. Compounds according to the invention can be administered by any suitable method, including without limitation, by gels, capsules, tablets, IV, IP and/or directly to the tumor.

Gels can contain for example 2-4% (e.g., 3%) active compounds of the invention, such as compound 2250, alone or in combination with taurolidine/taurultam which also can be administered and present alone, and can be for topical administration. Such gels can be used to treat tumors of the skin and mouth, including squamous cell tumors of the mouth and skin. Such gels also can be used to treat cervical cancer or cervical dysplasia by being administered in a suppository to the vagina, or by syringe. The invention may include the combination of a suppository carrying an active compound.

Cutaneous squamous cell carcinoma (cSCC) poses a notable threat with its ability to form cutaneous in-transit metastases (>2 cm away from primary tumor) and regional lymph node metastases, followed by distant metastases, associated with a very poor prognosis and median pathology-related mortality rate of >70%. An appropriate systemic treatment for metastatic cSCC is still controversial and remains unclear. Most commonly used therapies in this setting are unspecific cytotoxic chemotherapies mainly using cisplatin and/or 5-fluorouracil and radiotherapy (alone or in combination), even though long-term curative chemotherapeutic data are still lacking. These therapies are associated with numerous serious side effects and adverse effects including but not limited to nausea, vomiting, fever, myelosuppression, severe involvement of tissues including neurotoxicity, hepatotoxicity, nephrotoxicity, and ototoxicity. These side effects can form a contraindication for chemotherapy treatments, considering that the concerned target population is diagnosed with metastatic SCC at a mean age of 70 years and often suffers from significant comorbidities. Immunotherapies such as PD-1 blockade induces a response in approximately half the patients, but is associated with adverse events (diarrhea, fatigue, nausea, constipation) that usually occur with immune checkpoint inhibitors.

Figure 12A:
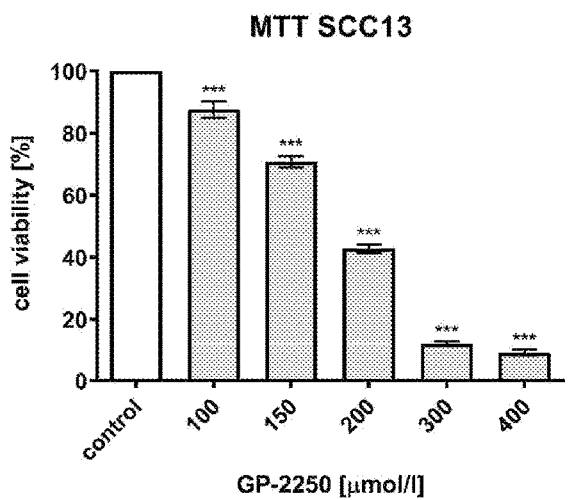
FIGS. 12A and 12B show the effects of GP-2250 in different cSCC cell lines, measured by MTT assay.

The present disclosure provides compounds and methods for inhibiting cSCC cell growth and proliferation. The present disclosure provides compounds and methods for avoiding one or more serious side effects and adverse effects disclosed herein. As exemplified in Example 11, compounds of the present disclosure may provide a dose-dependent effect in treating cSCC. For example, increasing concentrations of compound GP-2250 led to significant and subsequently increasing antineoplastic effects compared to the untreated control groups in all carried out assays after 24 hours: the maximal achieved viability reduction in A431 cells was 95.80% (±0.47) (FIG. 12B) and in SCC13 cells 91.18% (±0.99) (FIG. 12A).

Compounds of the present disclosure are useful in methods of inhibiting cancer cell proliferation, reducing cancer cell motility reduction, and inducing apoptotic and necrotic cell death. For example, as shown in the data provided herewith, GP-2250 inhibited proliferation, reduced cell motility reduction, and induced apoptotic and necrotic cell death. Same proportional dose-effect pattern of substance GP-2250 was detected after 24 hours in anti-proliferative effects of BrdU analysis (FIGS. 13A-13B), FCM analysis (FIGS. 14A-14F) and observed in anti-migratory effects in cell migration assays, during 24 hours with intermittent measurements (FIGS. 15A-15D). All the highest tested concentrations of GP-2250 (400 µmol/l for SCC13 and 200 µmol/l for A431 cells) lead to pronounced antineoplastic, anti-proliferative and apoptotic effects in all assays, significantly greater than lower administrated concentrations and compared to untreated controls. In some aspects, the present disclosure includes administering the compounds of the present disclosure in combination with Cemiplimab-rwlc, Pembrolizumab, Cemiplimab-rwlc, fluorouracil, imiquimod, vismodegib, sonidegib, avelumab, or other immunotherapies or chemotherapies. In some aspects, the present disclosure includes reducing side effects of administration of one or more of Cemiplimab-rwlc, Pembrolizumab, Cemiplimab-rwlc, fluorouracil, imiquimod, vismodegib, sonidegib, and avelumab therapy by administering the compound of the present disclosure in combination with a reduced dosage of one or more of Cemiplimab-rwlc, Pembrolizumab, Cemiplimab-rwlc, fluorouracil, imiquimod, vismodegib, sonidegib, and avelumab therapy.

Surprisingly, minimum concentrations of 100 µmol/l GP-2250 in SCC13 cells and 50 µmol/l GP-2250 in A431 were observed to be the lowest doses capable of significantly reducing cell viability and inhibiting proliferation rates in both cell lines. Comparing these dosages of GP-2250 to the ones found in the study of Buchholz at al. (Innovative substance 2250 as a highly promising anti-neoplastic agent in malignant pancreatic carcinoma—in vitro and in vivo. BMC Cancer. 2017 Mar. 24; 17(1)) with comparable assays, similar study design and analogue handling of the assays (i.e. cell density, incubation time, measurements), it was found that the effect-related concentrations used in this study are much lower. Buchholz at al. showed comparable effects analyzing the effect of substance GP-2250 on five different human pancreatic cancer cell lines (AsPC-1, BxPC-3, MiaPaca-2, Panc-1, Panc-Tu1) with a higher concentration range from 100 to 2000 µmol/l. In the Buchholz report, at a concentration of 1000 µmol/l more than 50% reduction of viable cells was monitored in four out of five cell lines.

The present disclosure also demonstrated was found that SCC13 cells require higher concentrations of GP-2250 than A431 cells in order to achieve comparable antineoplastic, anti-proliferative and apoptotic effects among the assays of the two cSCC cell lines (Table 2).

TABLE 2

Results of MTT and BrdU assays of GP-2250 in both cSCC cell lines (SCC13 and A431)

|  | SCC13 | A431 |
| --- | --- | --- |
| MTT cytotoxicity assay | 42.74 (±1.43) | 4.20 (±0.47) |
| BrdU proliferation assay | 62.40 (±1.11) | 32.85 (±2.52) |

Table 2: Results are represented as mean value in % (±SD in %) of viable cells in the MTT assay and of proliferated cells in the BrdU assay for concentrations of 200 µmol/l GP-2250

Analyzing both cell lines offers a possible explanation to the divergence in cell responses, elucidating small differences between their origins and characteristics. Both cell lines are human, epidermal squamous carcinoma cells. While A431 cells are originally derived from a 85-year-old female patient and characterised by p53-deficiency (23), SCC13 cells are derived from a primary facial cSCC tumor of a 56-year-old female patient and are p53—also p16-deficient, probably enhancing a quicker tumor cell replication, hence tumor proliferation. Differences in dose-related effectiveness between SCC13 and A431 may further be due to inherent differences in cell turnover, unequal expression of EGFR and sensitivity to reactive oxygen species (ROS). Excessive ROS production during mitochondrial oxidative metabolism can lead to oxidative stress and macromolecular damage in cancer.

Flow cytometry (FCM) analysis displayed in all cSCC cell lines a dose-response correlation concerning relative distributions of viable, apoptotic and necrotic cells. Increasing concentrations of GP-2250 caused a decrease of viable cells and an increase of apoptosis and necrosis, with a predominant contribution of apoptosis to cell death.

Apoptosis leads to a caspase-dependent cell destruction with DNA fragmentation and cell shrinkage or to caspase-independent cell destruction with subsequent phagocytosis of the apoptotic cells. Considered the lack of phagocytosis in a cell culture setting due to absence of inflammatory cells, a secondary necrosis follows, an autolytic process of cell disintegration, characterized by the same appearance of primary necrosis. The necrosis marker (PI) used in this study could ultimately not differentiate between a substance-induced primary necrosis or secondary necrosis—due to the lack of phagocytosis. The third type of programmed cell death, next to autophagy and apoptosis, which is amongst others activated through ROS, is programmed necrosis, causing cell swelling and membrane rupture.

ROS plays an important role in substance GP-2250 induced programmed cell death (PCD). ROS expression under one and the same treatment differs in intensity in the same cancer type depending on whether tumor tissues are extracted from metastatic or non-metastatic cancer cells.

The compounds of the present disclosure are useful for inhibiting or reducing cancer cell migration. In some aspects, the subject has a tumor, cancerous cells, pre-cancerous cells, or cancer stem cells, is suspected of having a tumor, cancerous cells, pre-cancerous cells, or cancer stem cells, or is at risk of developing a tumor, cancerous cells, pre-cancerous cells, cancer stem cells or metastases thereof, for example, due to genetic, environmental and/or vocational factors. In some aspects an effective dosage of the compounds of the present disclosure are administered to the subject to inhibit or reduce cancer cell migration in the subject. As explained in Example 12, a dose-dependent increase in inhibiting or reducing cancer cell migration was demonstrated.

Solid dosage forms for oral administration include capsules, tablets, pills, powders, and granules. In such solid dosage forms, the provided composition is mixed with at least one inert, pharmaceutically acceptable excipient and/or fillers or extenders (e.g., starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato starch, tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay), and lubricants (e.g., talc, calcium stearate, magnesium stearate, solid polyethylene glycols, sodium lauryl sulfate), and mixtures thereof. In the case of capsules, tablets and pills, the dosage form may comprise buffering agents.

The compounds of this disclosure, particularly compound 2250, have been found to be very soluble in water. In certain embodiments, no PVP necessary to increase the solubility. For example, a 3.2% solution 2250 is isotonic. This is an unexpected advantage over taurolidine.

Compounds of the invention, such as compound 2250 (with or without taurolidine and/or taurultam) are particularly useful in surgical oncology, since the compounds do not hinder wound healing. Administration of other antineoplastic drugs must be delayed for up to five weeks or more after surgery because other such antineoplastic drugs hinder wound healing and promote anastomotic leakage. Such problems can be avoided with compounds of the invention such as compound 2250, which can be administered during surgery and immediately thereafter, without wound healing issues or leakage issues.

Solid compositions of a similar type may be employed as fillers in soft and/or hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the provided composition(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

In certain embodiments, capsules may contain an excipient formulation containing one or more of hydroxypropyl methylcellulose (HPMC), gelatin, and fish gelatin. In certain embodiments, a capsule may contain compound 2250 in combination with taurolidine and/or taurultam. The capsule may optionally further contain one or more of lycopene, ellagic acid (polyphenol), curcumin, piperine, delphinidin, resveratrol, isothiocyanates such as sulforaphane, capsaicin, and piperlongumine.

Active compounds of the invention, such as compound 2250, can be combined with compounds such as gemcitabine. This combination can be used to treat cancers, such as pancreatic cancer. Taurolidine and/or taurultam also can be combined with gemcitabine to treat, for example, pancreatic cancer.

In some embodiments, a nutritional cancer prophylaxis and treatment product may contain 100-500 mg compound 2250 alone or in combination with 100-500 mg taurolidine and/or taurultam and one or more of lycopene, e.g., 20-200 mg, ellagic acid (polyphenol), curcumin, piperine (20-200 mg), delphinidin, resveratrol, isothiocyanates such as sulforaphane, capsaicin, and piperlongumine.

It was unexpectedly found that the compounds could be administered during surgery and immediately after surgery because the compounds do not inhibit wound healing like other chemotherapy agents.

It was unexpectedly found that taurolidine, taurultam, and oxathiazin-like compounds and derivatives thereof kill tumor stem cells, which is very unusual and perhaps unknown among chemotherapy agents. Typical chemotherapy agents, if effective against tumor stem cells, generally are only effective at very high doses which are extremely toxic to human patients.

It was unexpectedly found that lower doses of taurolidine and/or taurultam killed tumor stem cells than were needed to kill tumor cells.

It was unexpectedly found that Oxathiazin-like compounds and derivatives thereof have a half-life in human blood that is significantly longer than the half-life of taurolidine and taurultam. Accordingly, these compounds are cleared less rapidly from the bloodstream of the patients, thereby effectively delaying loss of drug potency caused by the body's clearance mechanisms.

It was unexpectedly found that certain Oxathiazin-like compounds and derivatives thereof have reduced burning sensation when applied directly into tissue, unlike this effect observed in patients treated with taurolidine.

It was unexpectedly found that the Oxathiazin-like compounds and derivatives thereof have a particularly advantageous combination of properties including high water solubility, versatile administration routes including oral and i.v., extended stability and half-life, and reduced side effect of burning sensation.

Thus, the half-life of compound 2250 is greater than 24 hours in human blood, which is significantly higher than the half-life of taurolidine, which was found to be ~30 minutes using the same test.

In one embodiment, the invention includes treating a patient by administering compound 2250 to the patient that results in a baseline blood concentration of compound 2250 within about 5 minutes of administration. The method involves maintaining a blood concentration of compound 2250 in the patient that is about 80% of the baseline blood concentration for about 20 hours.

In one embodiment, the invention includes maintaining a blood concentration of an anti-neoplastic compound in a patient that is about 80% of the patient's baseline blood concentration for about 20 hours by administering a daily dosage of compound 2250 once daily to maintain the blood concentration that is 80% of the baseline blood concentration.

The daily dosage may be about 0.1 g to about 100 g, e.g., about 5 g to about 30 g. The daily dosage may be administered in the form of an orally administrable composition. The daily dosage may be administered in the form of a capsule, a tablet, or a pharmaceutically acceptable solution. The daily dosage may be administered in a form that contains compound 2250 at a concentration of about 0.01 to about 3% w/v. The daily dosage may be administered in a form that contains compound 2250 at a concentration of about 0.01 µg/ml to about 1000 µg/ml. The daily dosage may be administered in a form that contains one or more solubilizing agents, e.g., polyols.

In some embodiments, the compounds are administered in compositions at a concentration of about 0.01 to about 1000 µg/ml. In some embodiments, the compounds are administered in compositions at a concentration of about 1 to about 100 µg/ml. In some embodiments, the compounds are administered in compositions at a concentration of about 10 to about 50 µg/ml. The composition may also contain about 0.01 to about 1000 µg/ml, about 1 to about 100 µg/ml, or about 10 to about 50 µg/ml taurolidine and/or taurultam.

In some embodiments, the compounds are administered in compositions at a concentration of about 0.01 to about 3%. In some embodiments, the compounds are administered in compositions at a concentration of about 0.1 to about 2.5%. In some embodiments, the compounds are administered in compositions at a concentration of about 1% to about 2%. The composition may additionally contain about 0.01 to about 3%, about 0.1 to about 2.5%, or about 1 to about 2% taurolidine and/or taurultam.

In one embodiment, the oxathiazin-like compounds and derivatives thereof may be administered as a co-therapy with taurolidine and/or taurultam to kill tumor stem cells. In accordance with such an embodiment, the co-therapy has been unexpectedly found to require a lower dosage of drug to kill tumor stem cells than necessary to kill normal tumor cells.

In certain embodiments, the oxathiazin-like compounds and derivatives thereof may be administered with Vitamin D3, which results to increase the anti-tumor effects of the compounds.

In one embodiment, the compound is administered to the subject at a total daily dose of from about 0.1 g to about 100 g, about 1 g to about 80 g, about 2 g to about 50 g, or about 5 g to about 30 g.

Effective dosage amounts of the compounds are dosage units within the range of about 0.1-1,000 mg/kg, preferably 150-450 mg/kg per day, and most preferably 300-450 mg/kg per day.

As used herein, the term pure refers to a substance that is at least about 80% pure of impurities and contaminants. In some embodiments, the term pure refers to a substance that is at least about 90% pure of impurities and contaminants. In certain embodiments, the term pure refers to a substance that is at least about 95% pure of impurities and contaminants. In some embodiments, the term pure refers to a substance that is at least about 99% pure of impurities and contaminants. In some embodiments, the term pure refers to a substance that is at least about 99.5% pure of impurities and contaminants.

In certain embodiments, compounds, compositions, and methods of the present invention encompass the use of micronized compounds. In some embodiments, the term "micronized" as used herein refers to a particle size in the range of about 0.005 to 100 microns. In certain embodiments, the term "micronized" as used herein refers to a particle size in the range of about 0.5 to 50 microns. In certain embodiments, the term "micronized" as used herein refers to a particle size in the range of about 1 to 25 microns. For example, the size of the drug particles may be about 1, 5, 10, 15, 20, or 25 microns.

In certain embodiments, compounds, compositions, and methods of the present invention encompass the use of nanoparticles. As used herein, the term "nanoparticle" refers to any particle having a diameter of less than 1000 nanometers (nm). In some embodiments, a nanoparticle has a diameter of less than 300 nm. In some embodiments, a nanoparticle has a diameter of less than 100 nm. In some embodiments, a nanoparticle has a diameter of less than 50 nm, e.g., between about 1 nm and 50 nm. Suitable formulations for injection or infusion may comprise an isotonic solution containing one or more solubilizing agents, e.g., polyols such as glucose, in order to provide solutions of increased compound concentration. Such solutions are described in EP 25366261. The solution can be rendered isotonic with ringer solution or ringer lactate solution. The concentration of the compound in such solutions may be in the range 1-60 g/liter.

In certain embodiments, exemplary compounds and processes for making compounds of the invention include the following:

The compounds may be in crystalline form, e.g., after crystallization and/or recrystallization in an alcohol, ketone, ester, or combination thereof. For example, the compounds of the present invention may be crystallized and/or recrystallized from an alcohol such as ethanol.

Exemplary compounds of the invention include the following:

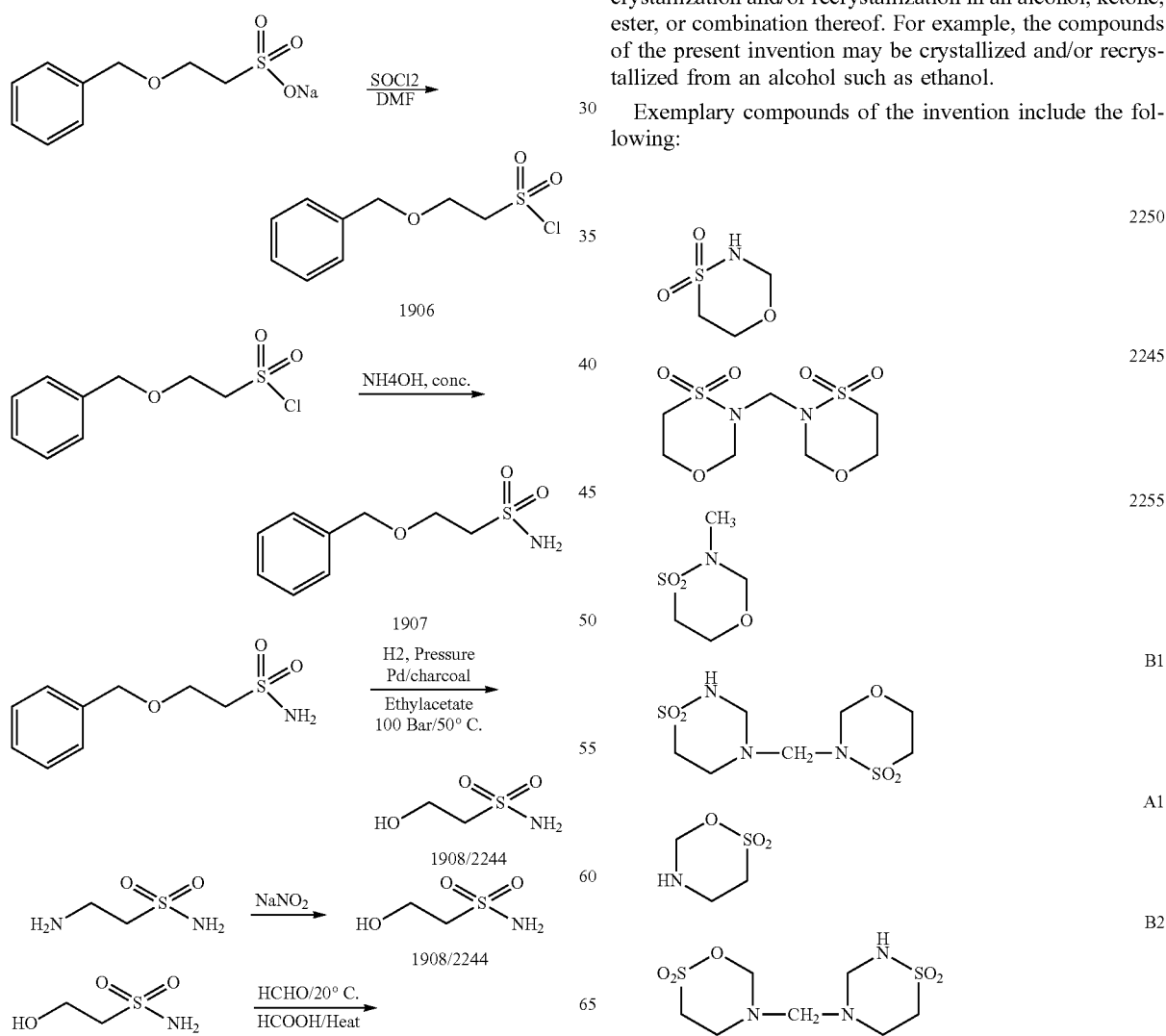

15
-continued

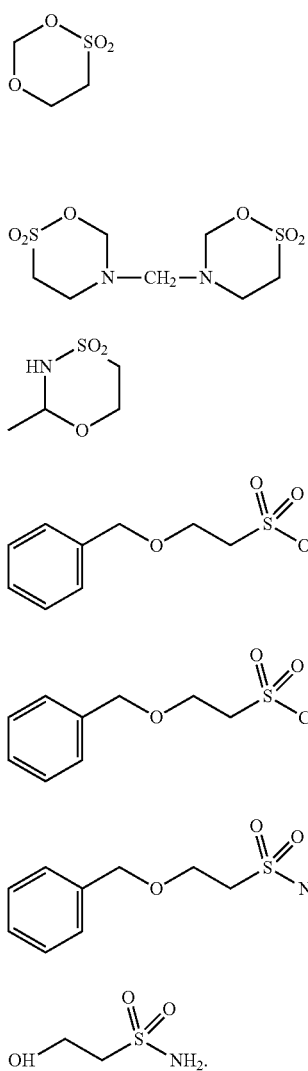

It has been found that when used in the form of nanoparticles, the compounds of the claimed invention achieve higher blood levels. In one embodiment, the present invention includes compound 2250 alone or in combination with taurolidine and/or taurultam. For example, the present invention includes nanoparticles of the compounds of the present invention encapsulated in capsules.

In certain embodiments, the invention also relates to derivatives of the above compounds having, e.g., activity as described herein of said compounds, for example, at least 25%, 30%, 40%, 50%, 60%, 70%, 80%, 90%, 95%, 100%, or more, of said activity.

In certain embodiments, the invention also relates to compositions containing the compounds described herein, including pharmaceutically acceptable solutions of said compounds, as well as orally administrable compositions such as capsules and tablets containing said compositions.

In certain embodiments, the compounds of the present invention can be administered to a subject or patient by any suitable means, for example, in solution, e.g., locally, systemically such as by intravenous infusion, or the like.

16
Synthesis of 2250 sublimes in a vacuum at ~70-80° C.
Starting Materials:
   Isethionic Acid,
   Carbylsulfat, Taurin, Taurinamide,
   Cysteine, Isethionic Acid, inter alia
Synthesis 1
I.
   a. Isethionic Acid via Carbylsulfate $CH_2=CH_2 + H_2SO_4 \mid SO_3 \longrightarrow$ $CH_2-OH$
$CH_2-SO_2-O-SO_2-OH$ $-H_2O$ Carbylsulfate $\xrightarrow{H_2O}$ $HO-CH_2-CH_2-SO_3H + H_2SO_4$ b. Isethionic Acid via Taurin
Biochemical synthesis via Cysteine, Taurin $HOOC-CH(NH_2)-CH_2-SH \xrightarrow{Oxidation}$ via Cysteinic acid Taurin + $CO_2$ Taurin $\xrightarrow{Biotransformation}$ Isethionic Acid Chemical Synthesis
   ethylenoxide with bisulfite
II. Isethionic Amide $HO-CH_2-CH_2-SO_2-NH_2$ a.

Taurinamide $\xrightarrow{NaNO_2}$ Isethioneamide (amido-isethionic)

$NH_2-CH_2-CH_2-SO_2NH_2 \longrightarrow$ $[O=N-NH-CH_2-CH_2-SO_2NH_2]$ $\downarrow$ $HO-CH_2-CH_2-SO_2-NH_2 + N_2$ b.

Carbylsulfate + $NH_3$

-continued
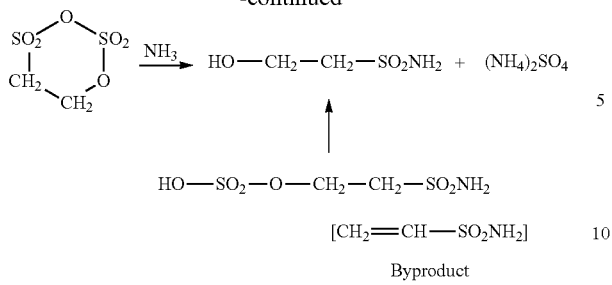
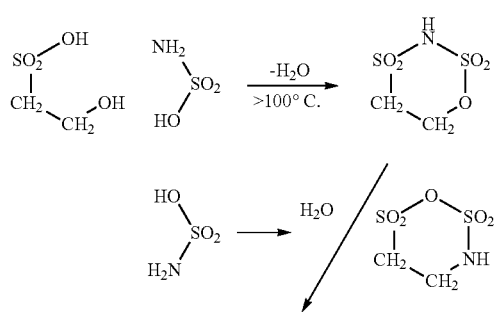
[CH₂=CH—SO₂NH₂]
Byproduct
Possible Alternative Chemical Synthesis Steps for 2250
a) Sulfamic acid
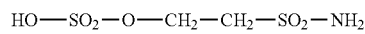
HO—SO₂—O—CH₂—CH₂—SO₂—NH₂
HO—CH₂—CH₂—SO₂—NH₂
HO—SO₂—O—CH₂—CH₂—SO₂—NH₂
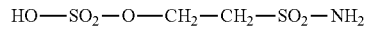  ↓ NaOH
CH₂=CH—SO₂—NH₂
(In presence of polymerization inhibitor)
↓ CH₂OCH₂(OH)₂
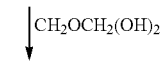
2250
b) Paraformaldehyde, Hexamethylenetetramine
(Hexamine, Formine, Urotropin)
c) 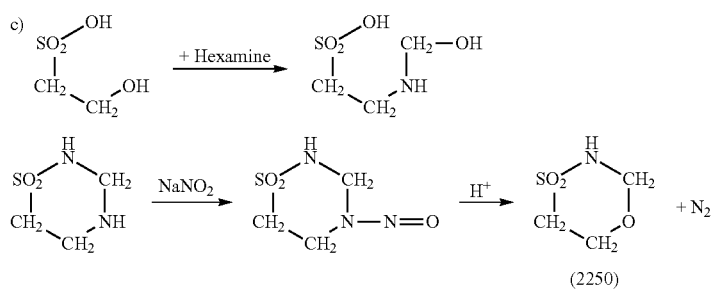
(2250)

-continued
d) 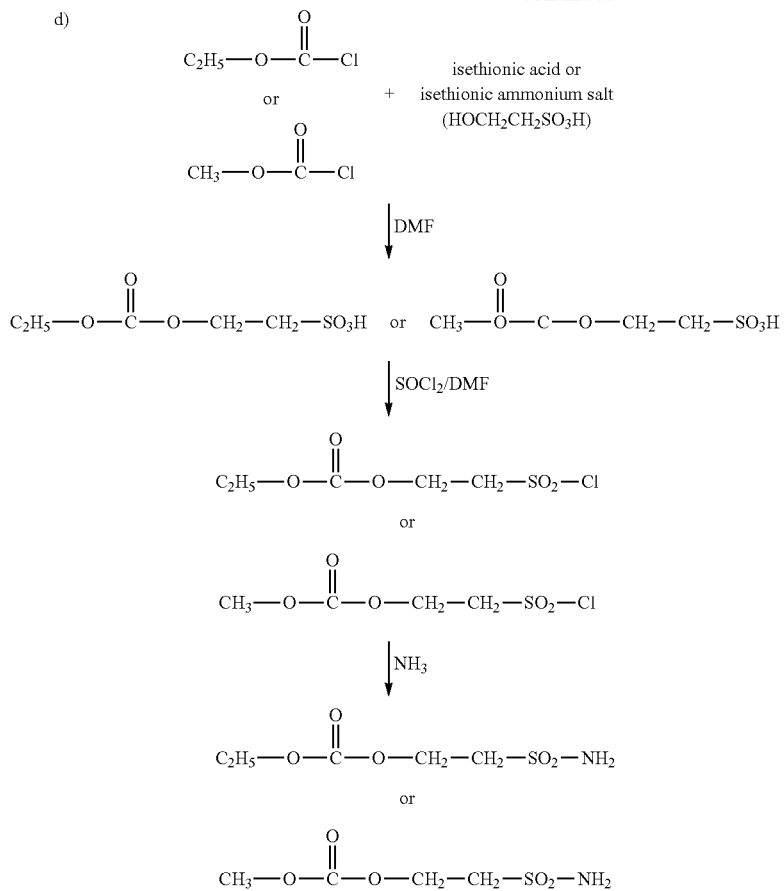
e)
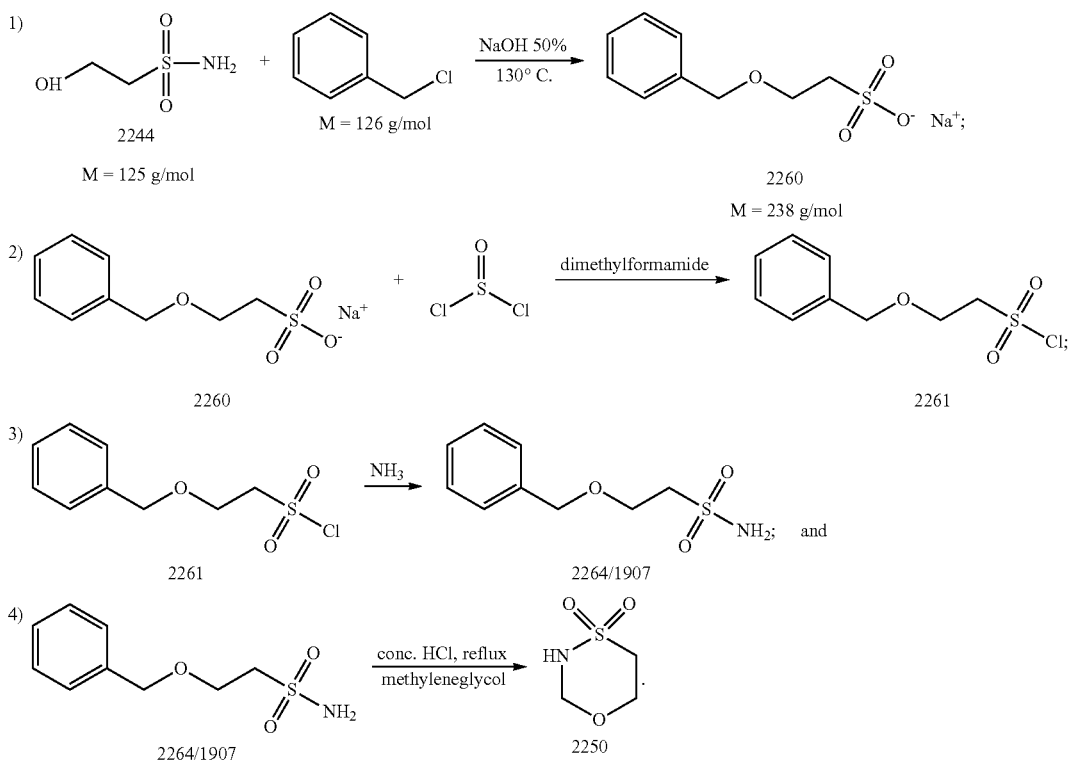

f)
1) 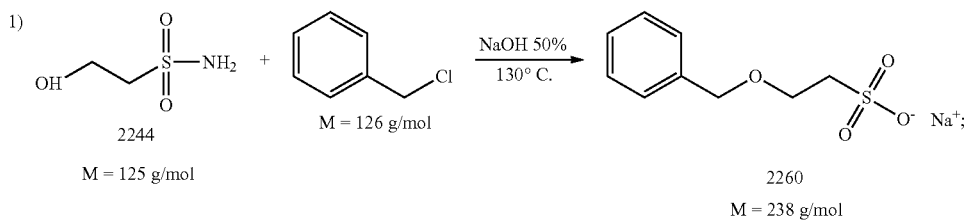
2) 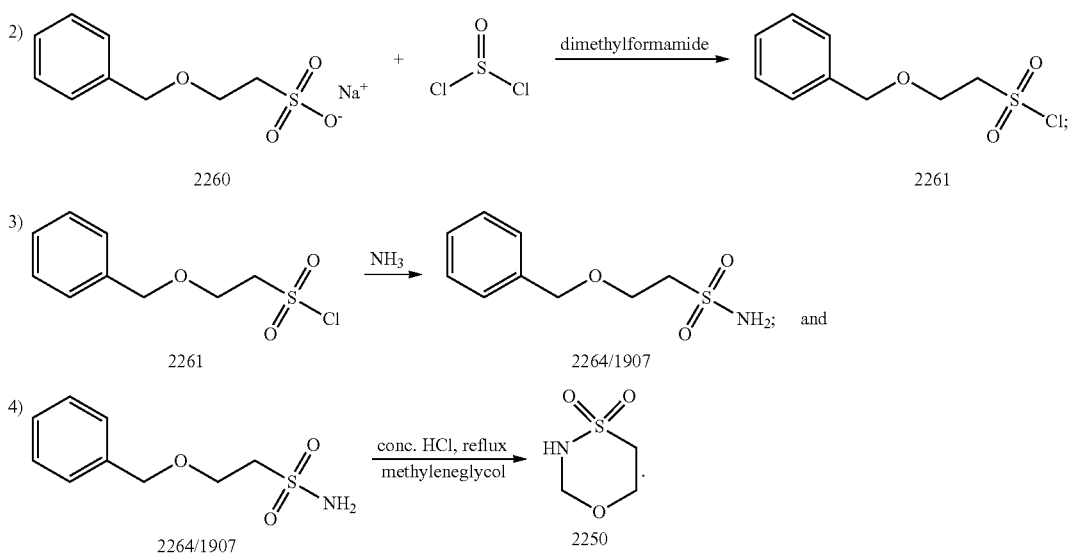
3)
4)
g)
1) 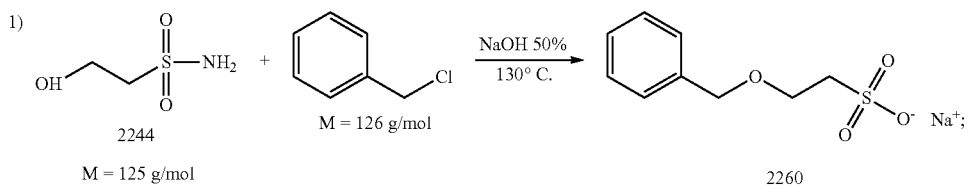
2) 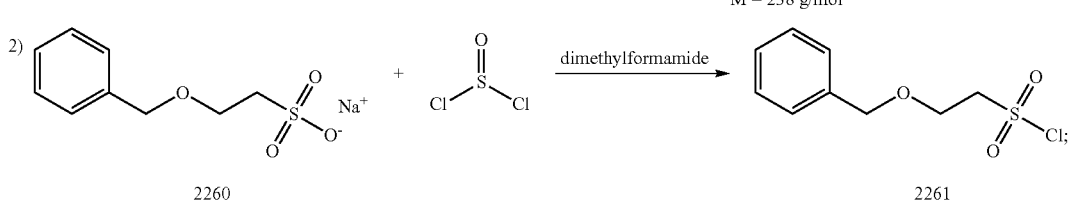
3) 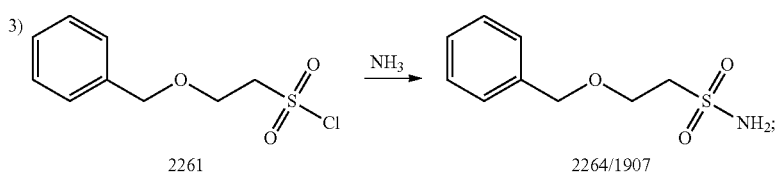
4) 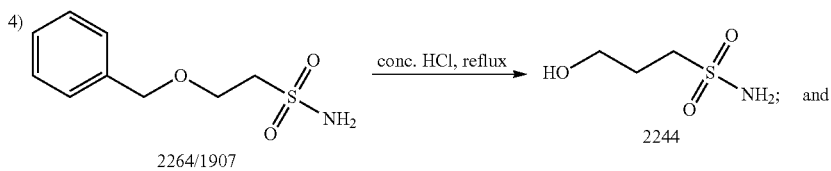

5)
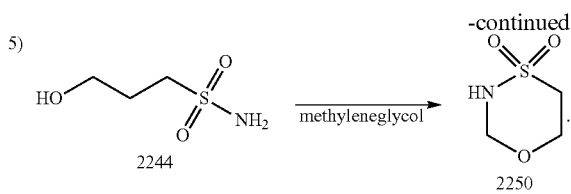
h)
1)
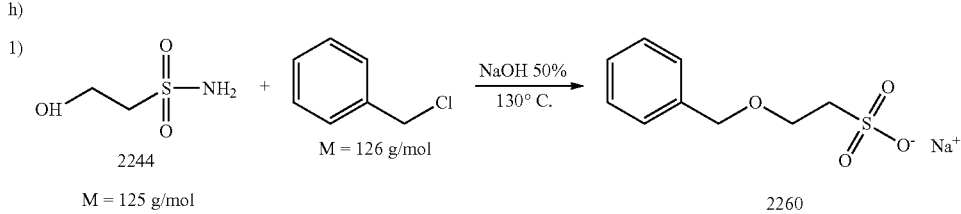
2)
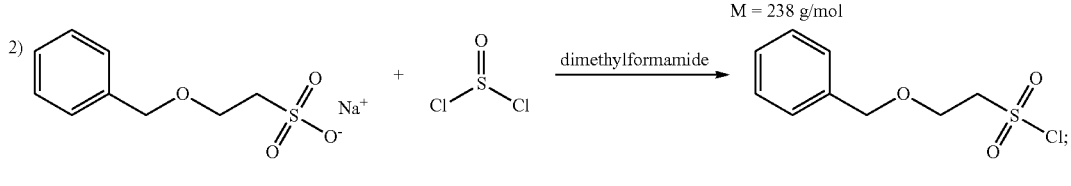
3)
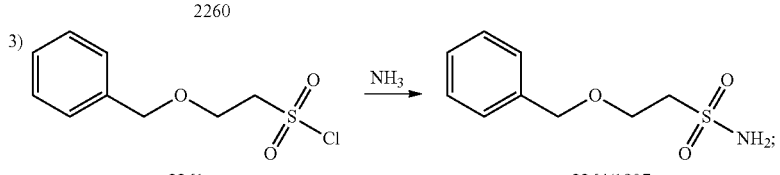
4)
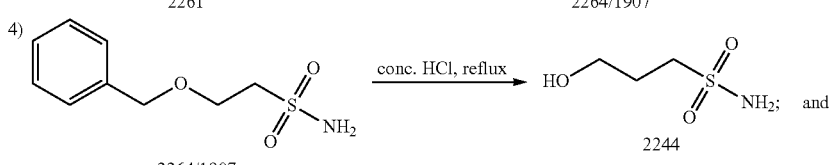
5)
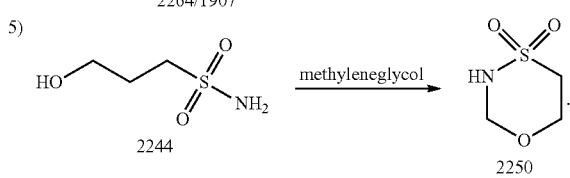
Several Alternative Synthesis Steps for 2250 and 2255
I. Starting materials 2250/2255
a.
Taurinamide $\xrightarrow{NaNO_2}$ Isethionicamide + $N_2$
b.
Carbylsulfate + $H_2O$
Ethionic acid
$\downarrow H_2O$
Isethionic acid
Synthesis sodiumisethionate from Ethylenoxide+Sodium-hydrogensulfite
Reaction of Amine with Carbylsulfate
II.
$R-NH-SO_2-CH_2-CH_2-O-SO_3Na$
$\downarrow H_2C(OH)_2$
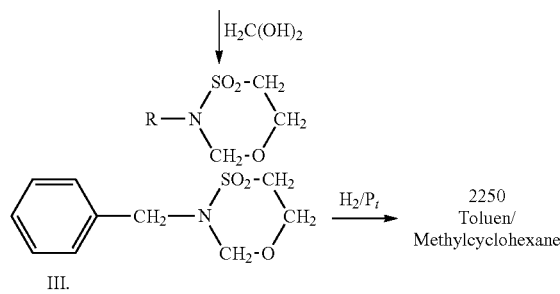
III.

-continued

2250 ⟶ +CH₂(OH)₂/HCOOH

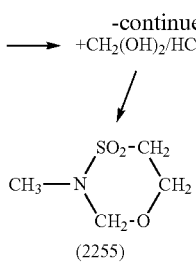

(2255)

Exemplary Synthetic Protocols

I. Synthesis of 2244

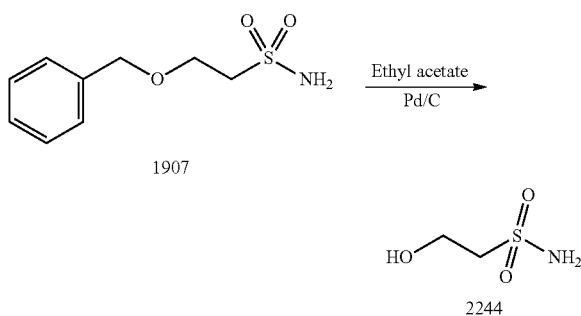

2.15 g of pure 1907 was dissolved in 100 ml acetic acid ethyl ester, and catalyzed using 0.5 g palladium on activated carbon. The solution was hydrogenated at room temperature and atmospheric pressure. The hydrogenation was complete after about 15 hours and the absorbed amount of hydrogen was 450 ml.

The hydrogenation was evacuated 3 times, each time with nitrogen, and then the reaction mixture was filtered through a filter aid (diatomaceous earth). The clear colorless ethyl acetate solution was concentrated and dried in a rotary evaporator.

Yield: 1.25 g, which was innoculated with crystalized 2244.

Melting point: 42-44° C.

IR: corresponds to 2244, 99.3% pure.

Synthesis of 2244

II.

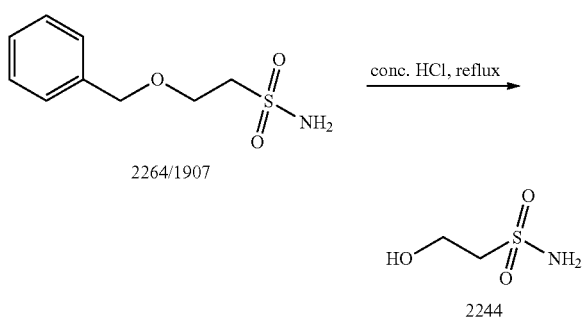

5 g (0.023 mol) of 2264/1907 was boiled in 50 ml of concentrated HCl for 3 hours under reflux, then allowed to cool to room temperature and separated with 30 ml of dichloromethane in a separating funnel. The aqueous phase was evaporated in a rotary evaporator and dried. A yellow oil remains which slowly crystallized after seeding with 2244 crystals.

IR corresponds to the substance 2244.
Recrystallized from ethyl acetate.
0.7 g obtained (24%).
Melting point: 44-45° C.
IR corresponds to the reference substance.

Synthesis of 2244

III.

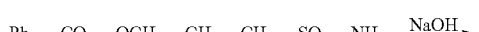

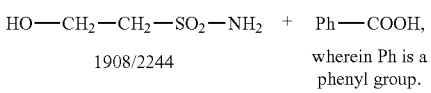

wherein Ph is a phenyl group.

230 mg 2269 was dissolved in 2 ml NaOH (1 N) and refluxed at boiling with a reflux condenser for 15 minutes. The clear solution was cooled to 20° C. and acidified with hydrochloric acid. The resulting precipitate was filtered off under vacuum and dried.

Yield: 110 mg.

Melting point: 114-116° C.

IR showed 99% benzoic acid as by-product.

The acidic solution was concentrated to dry it on a rotary evaporator and the solid was boiled with acetic ester. The ethyl acetate solution was filtered and concentrated to dryness under vacuum.

Weight: 110 mg. Oil was contaminated with oil and the IR peak for 2244 (isethionic acid amide) was unclean.

The 110 mg was recrystallized from acetic ester.

Yield: 65 mg, Melting Point: 43-45° C.

IR corresponded to 52% 2244.

Synthesis of 2244

IV.

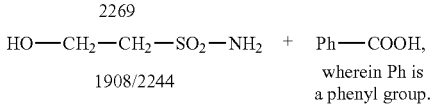

wherein Ph is a phenyl group.

1.15 g 2269 was dissolved in 10 ml NaOH (1 N) and refluxed at boiling for 15 minutes. The clear solution was cooled to 20° C. and acidified with hydrochloric acid. The resulting precipitate was filtered off under vacuum and dried.

Yield: 0.5 mg.

Melting point: 114-116° C.

IR showed 82% benzoic acid by-product as control substance. Hydrolysis is not complete.

The acidic solution was concentrated to dry it on a rotary evaporator and the solid was boiled with acetic ester. The ethyl acetate solution was filtered and concentrated to dryness under vacuum.

Weight: 0.8 g. Oil was contaminated with oil and the IR peak for 2244 (isethionic acid amide) was unclean.

The 0.8 g was recrystallized from acetic ester.

Yield: 160 mg, Melting Point: 43-45° C.

IR corresponded to 26% 2244.

Synthesis of 2244

V.

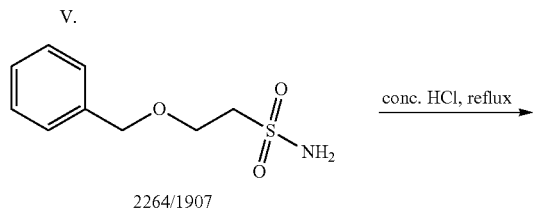

2264/1907

Figure 7:
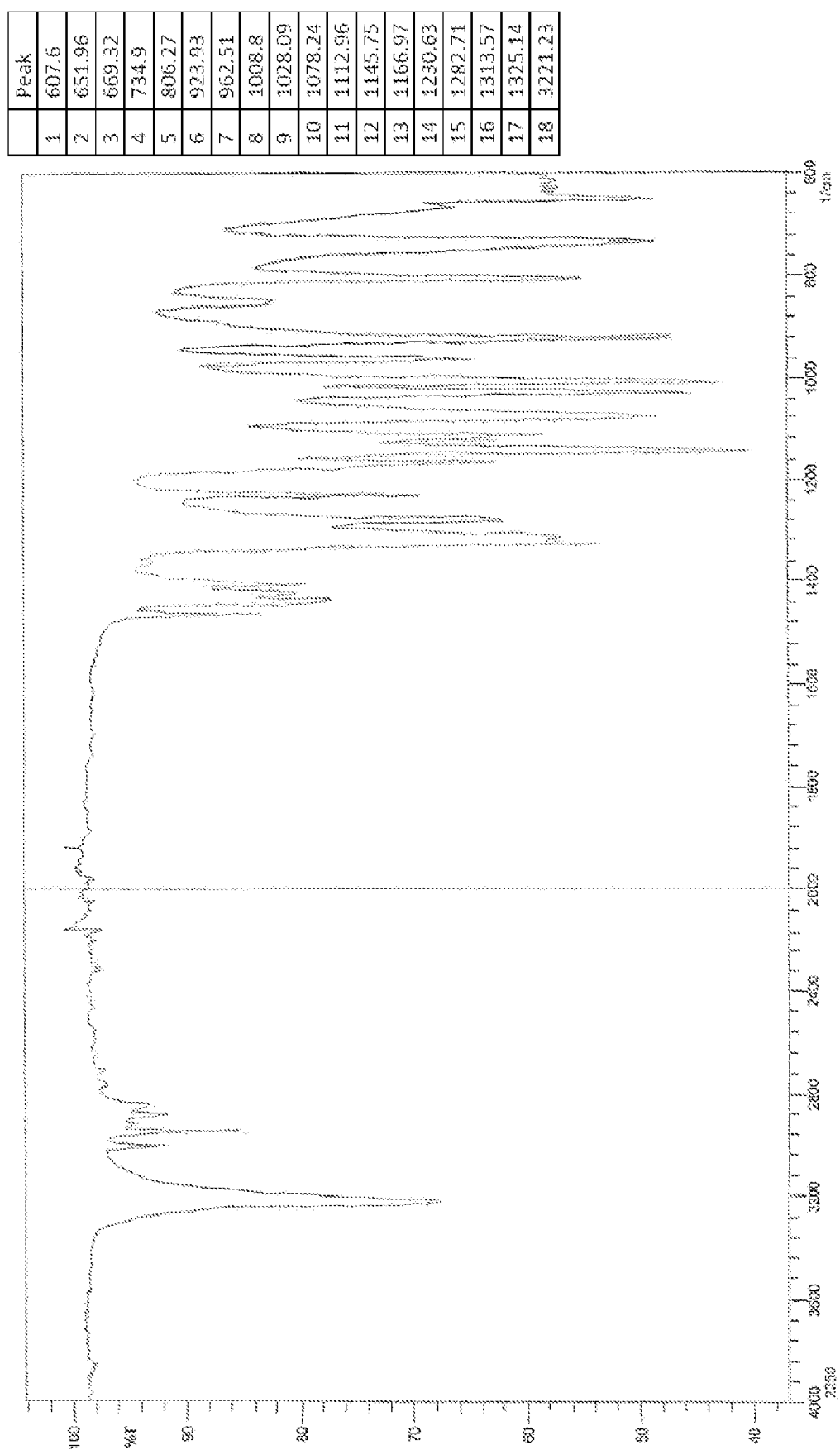
FIG. 7 FTIR spectrum of compound 2250 made according to the present invention.

215 g 0.1 Mol 2264 and 1000 ml of concentrated hydrochloric acid (ca. 36%) were boiled together for 30 minutes under reflux. The 2264 resolved and there was an oily layer. The reaction mixture was allowed to cool and transferred to a separatory funnel where the oil was separated from the water phase. The acidic aqueous solution in which should be solved isethionic acid amide (2244) was concentrated at 50° C. in a rotary evaporator almost to dryness. The yellow oily residue was placed overnight in the refrigerator and 32.3 g of clear crystals were filtered off under vacuum. Mp 43-45° C. IR: in oxygen having peaks at the following wave numbers 655.82, 729.12, 844.85, 898.86, 947.08, 1003.02, 1060.88, 1134.18, 1236.41, 1288.49, 1317.43, 1408.08, 1572.04, 3105.5, 3209.66, 3313.82, and 3427.62 cm$^{-1}$ as shown in FIG. 7.

The mother liquor was concentrated to complete dryness.

Synthesis of 2244

VI.

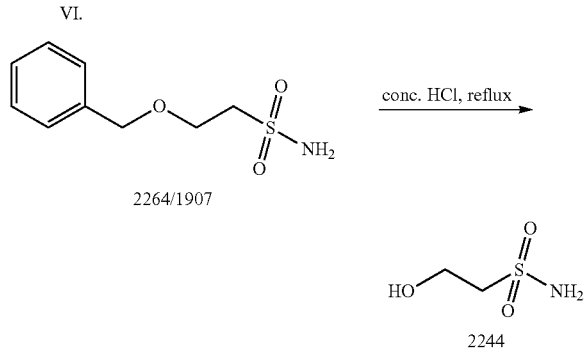

2264/1907

21.5 g 0.1 Mol 2264 and 100 ml of concentrated hydrochloric acid (ca. 36%) were boiled together for 30 minutes under reflux. An oily layer formed and the reaction mixture was allowed to cool in a separatory funnel where the oil was separated from the water phase. The acidic aqueous solution in which the isethionic acid amide (2244) was dissolved and shaken 2 times with methylene chloride, the methylene chloride was separated, and the acidic water solution was concentrated in a rotary evaporator at 50° C. to dryness. The yellow oily residue was placed overnight in the refrigerator and 12.3 g of oil was obtained. Mp.: 41-43° C. Analysis of the product showed that corresponds 99.8% to 2244 by IR.

Distillation Experiment:
12.3 g were distilled under high vacuum:

| Outside Temperature | Inside Temperature | Vacuum |
| --- | --- | --- |
| 190-210° C. | 183-186° C. | 0.1 mm |

Weight: 9.3 g of oil which was solid at room Temperature
Mp: 43-45° C.

Synthesis of 2244

VII.

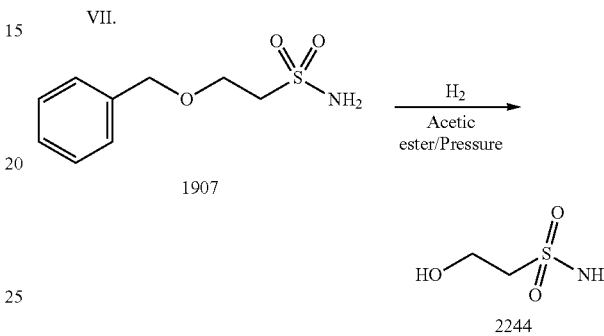

2.0 g of pure compound 1907 was dissolved in 200 ml acetic ester and 0.5 g palladium/activated carbon was added and the mixture was autoclaved at 100° C. and hydrogenated at 50° C. After 6 hours run-time, the reaction mixture was allowed to cool overnight, and was then filtered and concentrated to dryness under vacuum.

Wt.: 1.7 g oil—added CH2Cl2 and shaken, then allowed to stand—then suction filtered result in crystalline solid having Wt.: 0.6 g, melting point ca. 40° C.

For analysis 0.2 g of two-times acetic ester was added to crystallize. Melting point 43-44° C.

Synthesis of 2244

VIII.

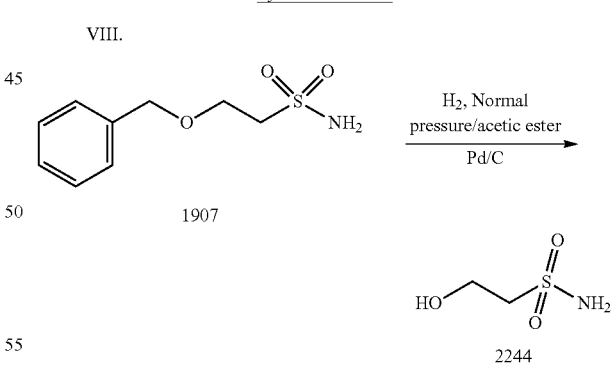

2.15 g of pure 1907 was dissolved in 100 ml acetic acid-ethyl ester, then added to 0.5 g palladium/activated carbon. Then the mixture was hydrogenated at room temperature and atmospheric pressure. Hydrogenation was terminated after approximately 15 hours. The absorbed amount of hydrogen was approximately 450 ml. The hydrogen was then evacuated 3 times and flushed with nitrogen, and then each reaction mixture was filtered through diatomaceous earth (celite). The clear, colorless solution, ethyl acetate was evaporated to dryness on a rotary evaporator.

Wt.: 1.25 g oil which crystallized after seeding with 2244 crystals.
Melting point: 42-44° C.
IR: corresponds to 99.3% 2244.

Synthesis of 2250

IX.

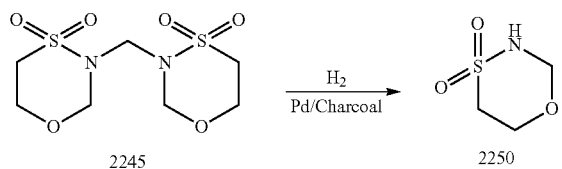

1.2 g pure 2245 pure was dissolved in 150 ml acetic acid purely solved at 60° C. 0.3 g of palladium on activated carbon was added and was stirred at 75° C. and the mixture was hydrogenated at atmospheric pressure.
Hydrogenation was stopped after 7 days. The absorbed amount of hydrogen was approximately 480 ml.
The hydrogen was evacuated and purged 3 times with nitrogen.
Then the reaction mixture was filtered at 70° C. through a filter aid (Diatomaceous earth). The clear warm glacial acetic acid solution was cooled down to room temperature and white crystals were suction filtered.
Weight: 0.74 g, Melting Point: 225-227° C.
IR: 2245 corresponds to the starting material
The mother liquor was concentrated on a rotary evaporator to dryness.
Weight: 0.38 g of impure material was extracted with ethyl acetate.
The solution was concentrated.
Ethyl acetate Soluble Portion: Semi-solid substance obtained by sublimation;
Obtained 0.15 g semi-solid substance that was recrystallized from a few drops of water
Yield: 70 mg, Melting Point: 95-98° C.
IR corresponded to 98% 2250.

1-step Synthesis in High Yield of Sodium 2-benzylether ethanesulfonate

X.

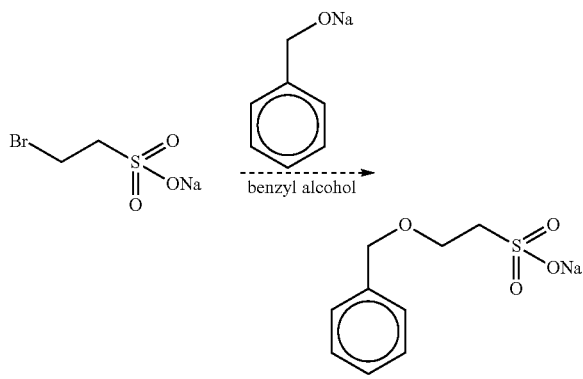

10.5 g sodium 2-bromoethanesulfonate was added to a solution of 110 ml benzyl alcohol and 1.15 g sodium benzyloxide.
Then the mixture was boiled under reflux four times. The mixture was then concentrated under vacuum to dryness and then boiled with ethyl alcohol three times. The alcohol was filtered and concentrated to dryness.
The yield was 9.8 g and was confirmed by UV and IR.
Pure crystals were obtained by boiling the resultant sodium 2-benzylether ethanesulfonate in ethyl alcohol, filtering, then cooling the solution to crystallize pure sodium 2-benzylether ethanesulfonate crystals out of solution.

Synthesis of 2250

XI.

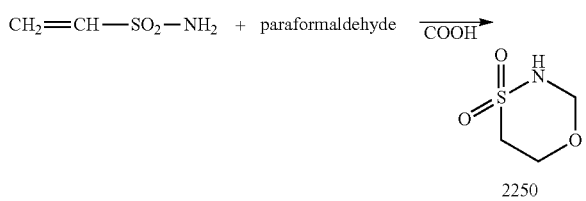

6.3 g vinylsulfonamide (from 2258),
50 ml of concentrated formic acid, and
1.1 g of paraformaldehyde were combined for 2 hours at reflux to produce compound
2250. Then, the clear acidic solution was concentrated on a rotary evaporator to dryness.
Residue is: 5.9 g of pale yellow, honey-like syrup.
IR: Mixture of vinylsulfonamide and 2250
A 2 grams was sublimated and a few crystals were obtained.
Sublimate semisolid: IR: corresponds to 98% 2250.

Synthesis of vinylsulfonamide

XII.

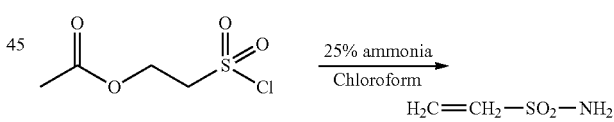

Formyl isethionic chloride was placed in 50 ml of chloroform and was placed in a 350 ml sulfonation flask and cooled to −10° C. Then 25% ammonia gas was introduced. After introduction of the ammonia gas, the weight of the chloroform/NH3 was found to be 5 g. From −3° C. to 2° C., the mixture was stirred slowly.
To 9.0 g distilled 2249
20 ml of chloroform was added drop wise. NH$_4$Cl precipitated immediately.
Then the ammonium chloride was filtered off under vacuum and the clear chloroform solution was concentrated in a rotary evaporator until dry.
Yield: 6.3 g of clear, thin oil.
IR: corresponds to 96% CH2=CH—SO2-NH2 (vinylsulfonamide).

Synthesis of 2261

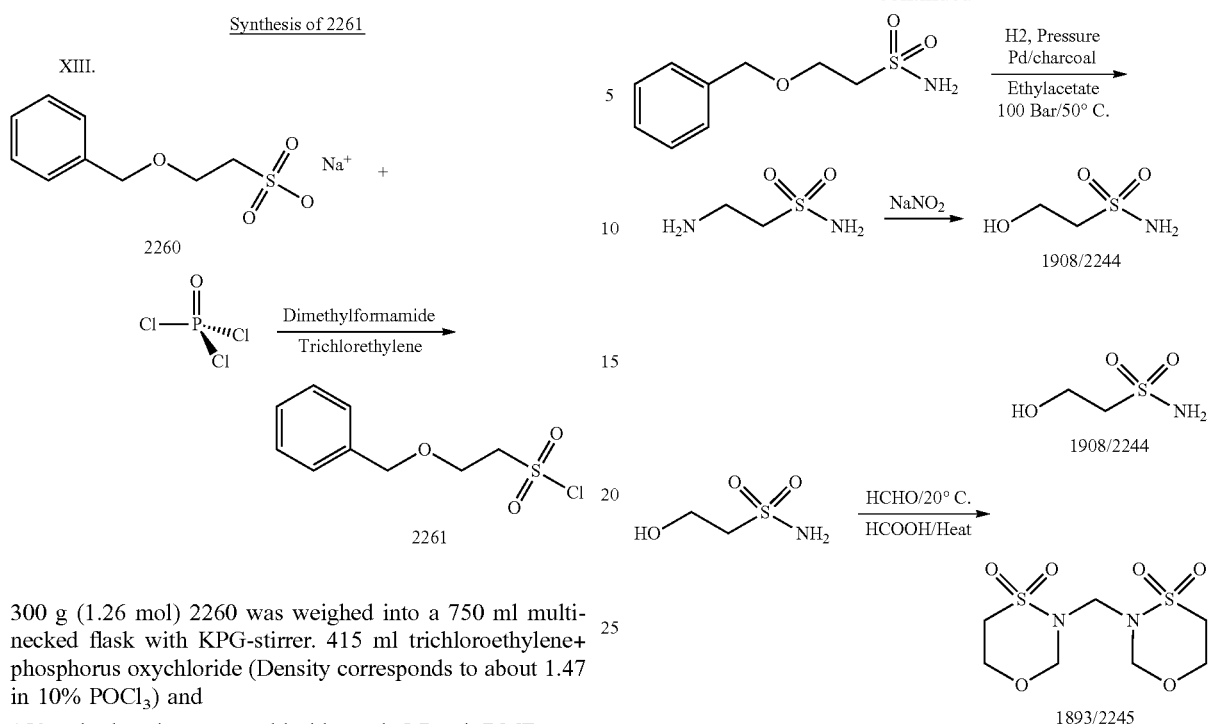

300 g (1.26 mol) 2260 was weighed into a 750 ml multi-necked flask with KPG-stirrer. 415 ml trichloroethylene+phosphorus oxychloride (Density corresponds to about 1.47 in 10% $POCl_3$) and 150 ml phosphorus oxychloride and 5.7 ml DMF was warmed to 105° C. while stirring. The mixture was allowed to react for 5 hours.

The solid was filtered by vacuum and the liquid was distilled under water-pump vacuum. The filter cake was washed with ethyl acetate. After distilling off of trichloroethylene and phosphorus oxychloride, the wash-acetate was transferred into a flask and also distilled. 250 g (1.07 mol-85%) of a yellow liquid was collected. IR corresponds to 2261.

Synthesis of 2250 and 2255

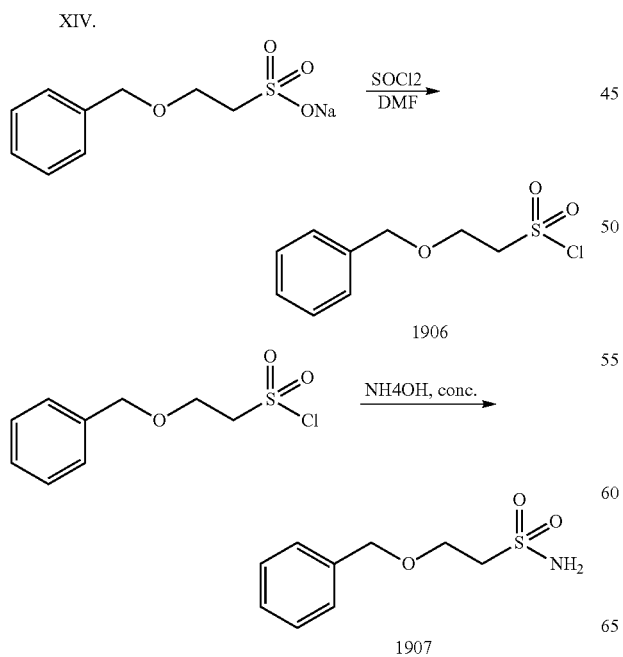

XV. New Synthesis Schemes for Compound 2250 and Related Compounds:

Starting Materials:

3-Hydroxypropane-1-sulfonic acid

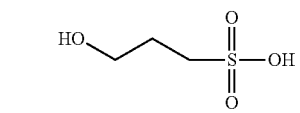

3-Hydroxy-propane-sulfonic acid-γ-sultone (1,3-Propane-sultone)

3-Hydroxy-propane-2-sulfonic acid

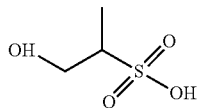

2-Hydroxy-propane-1-sulfonic acid

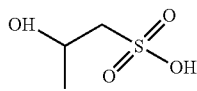

Compounds (Tetrahydro-oxathiazine-dioxide):

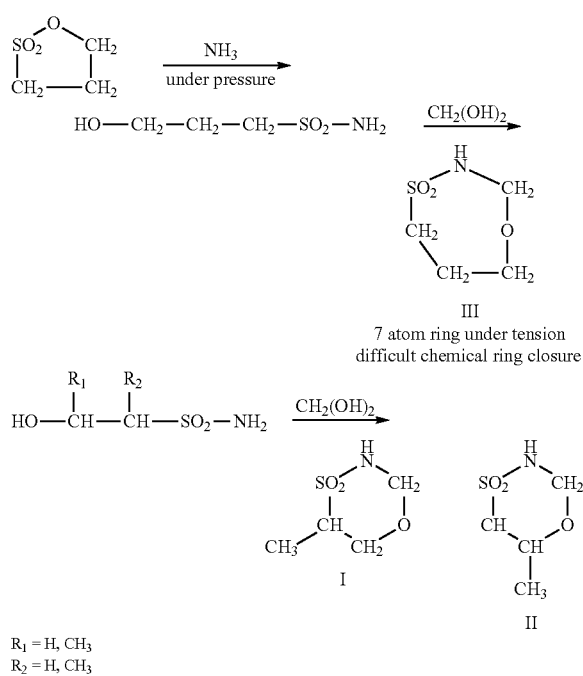

Chemical Intermediates
Protecting group: Benzyl chloride

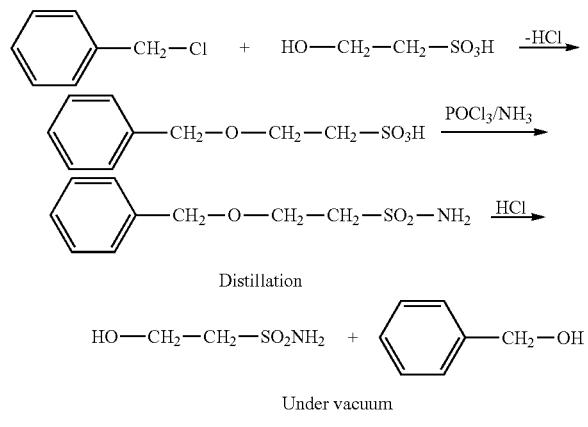

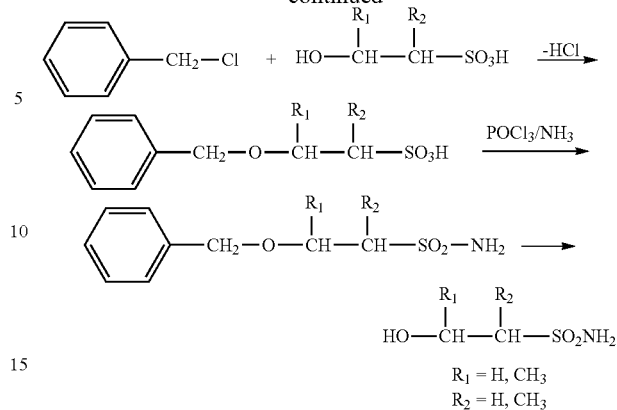

Protecting group: Benzyl chloroformate

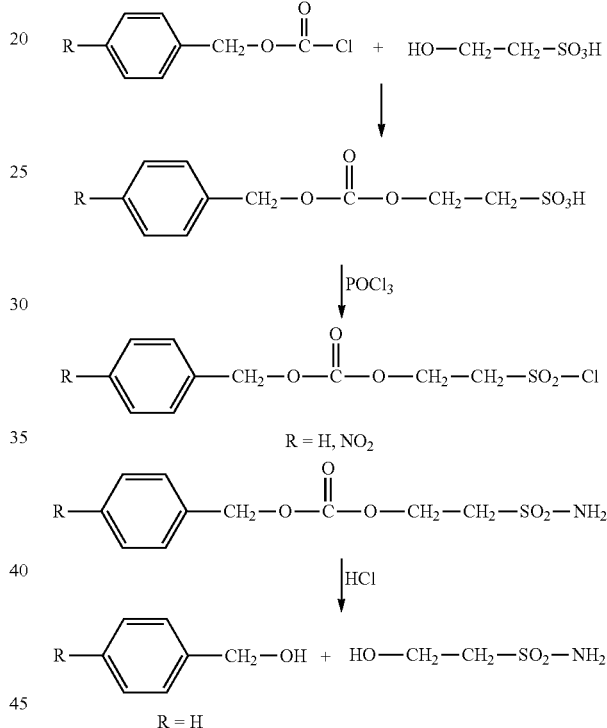

Synthesis of Precursor Compounds

XVI.

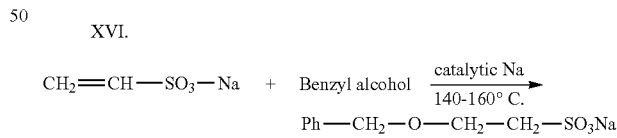

Synthesis:

83.9 g vinylsulphonic acid sodium was added to a solution of 400 ml benzylalcohol and 0.5 g sodium (catalytic amount) was added. The mixture was warmed with stirring to 150° C. and most of the vinylsulphonic acid sodium went into solution. After 3 hours, the mixture was allowed to cool overnight and a thick solid crystallized. This solid was vacuum-filtered and then suspended in ethyl alcohol, vacuum-filtered and dried.

Yield: 94.0 g, IR: corresponds to the desired compound (61.2% pure).

Synthesis of 1905

XVII.

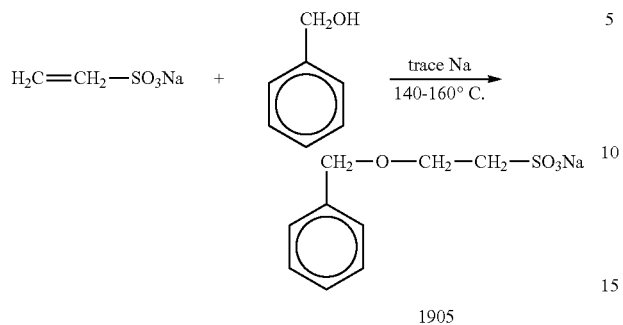

1905

60 grams of vinylsulfonic acid sodium were added to a solution of 1000 ml benzylalcohol and 0.5 g of sodium. Then, the whole mixture was stirred under reflux and heated. After approximately 3 hours, the excess benzyl alcohol was distilled and removed by vacuum and the rest was boiled with alcohol. The alcohol solution was filtered, concentrated, crystallized to about ½, 37.3 g of a yellow cotton-wool-like substance was obtained.

The procedure was also repeated with 250 g vinylsulfonic acid sodium and 2 liters of benzyl alcohol, processed as above and about 208 g was crystallized.

The procedure was also repeated with 100 g vinylsulfonic acid sodium and 1 liter of benzyl alcohol, processed as above and about 105 g was crystallized.

The procedure was also repeated with 200 g vinylsulfonic acid sodium, processed as above and about 130 g was crystallized.

Synthesis of 1906

XVIII.

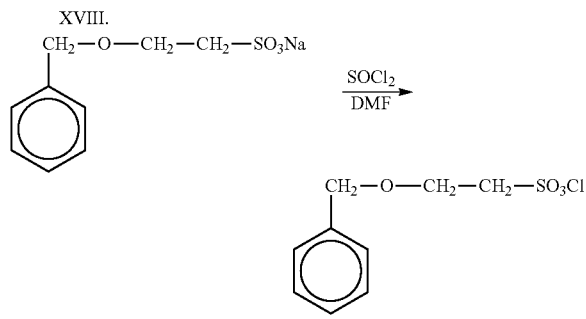

6.7 g of 1905 (recrystallized) was added to 50 ml thionyl chloride and 1 ml dimethyl formamide. The sodium salt dissolved immediately and the mixture was heated to 40-50° C., let stand overnight at 20° C. and vacuumed until concentrated. Yield: 9.8 g, which was added to 50 ml NaOH 2N and stirred well. The NaOH solution was washed with CHCl$_3$ and then shaken with concentrated HCl to precipitate and captured with Na$_2$SO$_4$, then dried and distilled.

The process was repeated with 208 g 1905 mixed with 1000 ml thionyl chloride and 10 ml dimethyl formamide. The mixture was refluxed and the excessive thionyl chloride was distilled off until dry. The yield was 250 g, which was processed as above.

Synthesis of 1907

XIX.

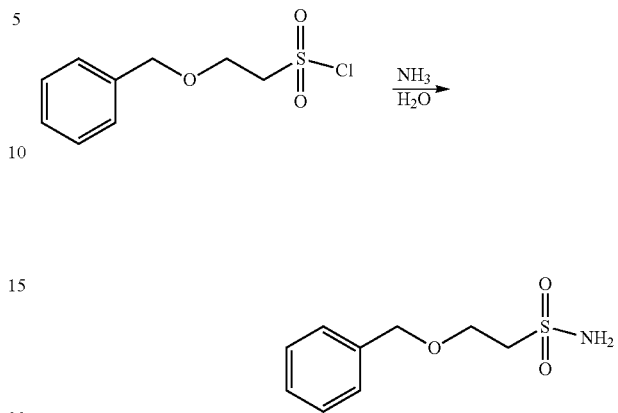

9.8 g of 1906 was dissolved in chloroform (CHCl3) (turbid) and concentrated into a portion of 150 ml concentrated ammonia in water and stirred. Stirring was continued for 3 hours with heating to 40-50° C. Then, the mixture was dried under vacuum and concentrated.

Yield: 3.1 g dark oil

The 3.1 g dark oil was added to 50 ml NaOH 2N and stirred well. The NaOH solution was washed with CHCl$_3$ and then shaken with concentrated HCl to precipitate and captured with Na$_2$SO$_4$, then dried and distilled. Yield: 2.5 g oil For analysis, a sample of 0.5 g was condensed at a temperature of 160° C., became solid and crystallized 3 times from ethyl acetate/benzene.

Melting point: 75-76° C.

Molecular formula: C$_9$H$_{13}$NO$_3$S

MW: 215.2

Calculated: C=50.23%, H=6.09%, N=6.51%, S=14.86%

Actual: C=50.14%, H=6.15%, N=6.35%, S=14.79%

Synthesis of 1908

XX.

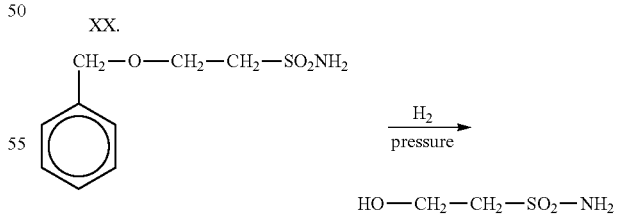

1.2 g of 1907 was dissolved in 200 ml ethyl acetate and 0.4 g Pd activated carbon was added. The mixture was hydrogenated in a hydrogenated autoclave at 100 and at 50° C. for 4 hours. The mixture was left under pressure for a weekend at room temperature. Then the ethyl acetate solution was filtered and dried under vacuum.

Yield: 1.1 g oil.

Synthesis of 1908

XXI.

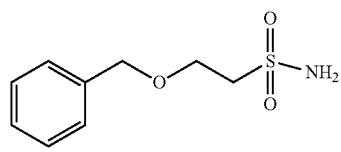

Chemical Formula: C₉H₁₃NO₃S
Molecular Weight: 215.27

$\xrightarrow{\text{H}_2}{\text{pressure/50° C.}\atop\text{ethyl acetate}}$

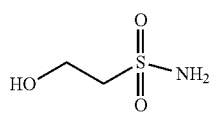

Chemical Formula: C₂H₇NO₃S
Molecular Weight: 125.15

2 grams of 1907 were dissolved in 200 ml ethyl acetate and 0.5 g Pd/Palladium/activated carbon was added. The mixture was hydrogenated in a high pressure autoclave at 100 and at 50° C. After 6 hours, the reaction mixture was left to cool overnight, then filtered and distilled under vacuum until it dried to a residual oil.
Yield: 1.7 g oil.
CH2Cl2 was added, agitated and allowed to stand, crystallized, and separated with suction under vacuum. Weight: 0.6 g, melting point about 40° C.
Analysis:
0.2 g recrystallized 2 times from ethyl actetate.
Melting point: 43-44° C.
Molecular formula: C₂H₇NO₃S
MW: 125
Calculated: C=19.22%, H=5.65%, N=11.21%, S=25.65%
Actual: C=19.20%, H=5.67%, N=11.07%, S=25.73%

XXII. Synthesis of 1909

19.9 grams of 1906 were dissolved in 100 ml chloroform and added into a solution of 23 grams pure benzylamine and 200 ml pure chloroform. Immediately, benzylamine hydrochloride precipitated and the reaction mixture became warm. The mixture was then refluxed and the hydrochloride compound was separated by suction and the clear CHCl3-mother liquor was put into vacuum for drying.
Yield: 27 g yellow clear oil that slowly became solid.
The 27 g was dissolved into about 20 ml ethyl acetate and N-hexane (q.s.) was added so that the solution became nearly turbid. The mixture was set aside in the cold overnight and it crystallized.
Yield: 9.2 g, melting point: 50-53° C.
For analysis, 1 g in N-hexane was recrystallized three times.
Melting point 56-57° C.

Synthesis of 2260

XXIII.

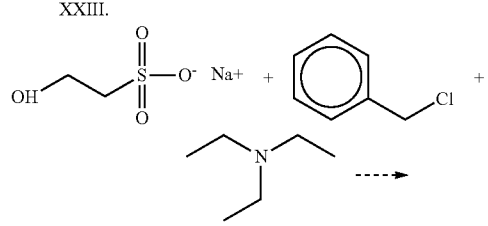

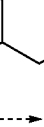

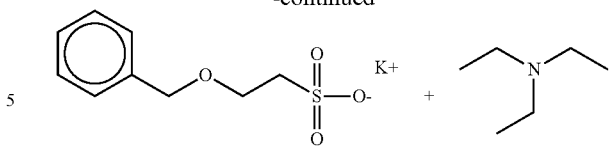

0.675 mol of isethionic acid sodium salt (100.0 g) and 2.02 mol benzylchloride (233 mL) were mixed in a 750 mL multi-necked flask with KPG-stirrer. The mixture was heated at 70° C. inside temperature (95° C. outside temperature) and then Triethylamine (120 mL) was added drop wise over one hour and the outside temperature was increased to 125° C. and maintained. Subsequently, outside temperature increased to 140° C., and the inside temperature rose to 130° C. A solid clustered at the stirrer, but went back into suspension. Hydrochloric acid vapors evolved.
30 mL of triethylamine was added drop wise and then reacted for 1.5 more hours. A viscous yellowish suspension formed. The product was allowed to cool to 50° C. inside temperature, then 300 mL water was added and vigorously stirred for 20 minutes and the mixture was transferred to a 2 L separatory funnel. Then, the flask was rinsed out with 100 mL of water.
The combined aqueous phases were washed twice with 280 mL dichloromethane.
The aqueous phase was held at 40° C., while KCl was added to the solution until saturated (about 130 g KCl). The mixture was filtered through a fluted filter and stored overnight in a refrigerator.
The remaining solid was extracted and dried, resulting in 30.85 g, yield of 17.9%.
IR: OH band is present, similar to the precursor.
The mother liquor was again treated with KCl and stored (at 35-40° C.) overnight in the refrigerator.
Solid from the second precipitation with KCl was filtered off and dried, resulting in 60.0 g=34.9% and the IR corresponds to the desired product.
Solid 1: Was boiled with 150 mL EtOH and filtered while hot.
By repeated precipitating with KCl, boiling and crystallization, 32 g of the product were obtained for a yield of 19%.

Synthesis of 2256

XXIV.

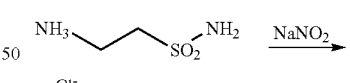

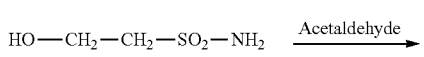

40 g taurinamide hydrochloride, 18 g Sodium nitrite and 300 ml of distilled water were boiled together under reflux until no more gas was created. The clear yellow solution was then cooled to 50° C.
30 ml of 1N NaOH was added to 10.5 g of acetaldehyde. The clear yellow solution was left over the weekend under vacuum to dry. The result was a rust-red honey-like residue weighing 37.6 g, which was extracted with ethyl alcohol. The alcohol solution was filtered and concentrated on a rotary evaporator to dry. The resulting dense oil residue was dissolved with ethyl acetate. The ethyl acetate solution was filtered, and concentrated. This resulted in 30.7 g of dense oil, rust-like color. From the dense oil, white crystals were isolated. The melting point is about 114-116° C.
The IR spectrum confirmed that the resulting compound had the structure of compound 2256:

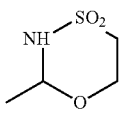

2256

In certain embodiments, a sublimation apparatus, comprised of laboratory glassware known in the art, may be used in a technique of sublimation to purify compounds according to the invention. In certain embodiments, a sublimation vessel is heated under vacuum and under reduced pressure. The compound volatizes and condenses as a purified compound on a cooled surface, leaving non-volatile residue impurities behind. This cooled surface often takes the form of a cold finger. After heating ceases and the vacuum is released, the sublimed compound can be collected from the cooled surface.

In one embodiment, substituted derivatives compound 2250 may be prepared. Substituted derivatives of compound 2250 include:

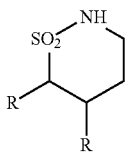

Wherein R may be H or alkyl or aryl. In certain embodiments, R is a $C_1$ to $C_6$ alkyl. In certain embodiments, R is methyl.

In certain embodiments, derivatives of compound 2250 are prepared according to the following reaction scheme:

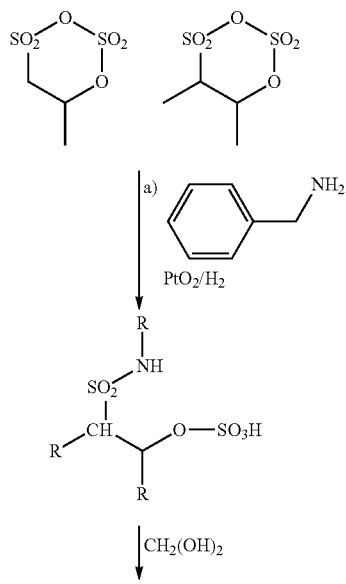

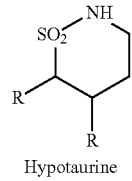

Hypotaurine

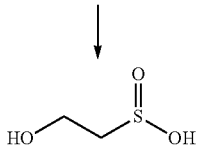

Chemical Formula: $C_2H_7NO_2S$
Molecular Weight: 109.15

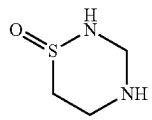

Chemical Formula: $C_2H_6O_3S$
Molecular Weight: 110.13

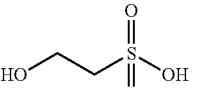

Chemical Formula: $C_3H_8N_2OS$       Chemical Formula: $C_3H_7NO_2S$
Molecular Weight: 120.17              Molecular Weight: 121.16
Hypotaurultam Chemical Formula: $C_2H_7NO_3S$
Molecular Weight: 125.15
Isethionic Amide esterification with formic acid

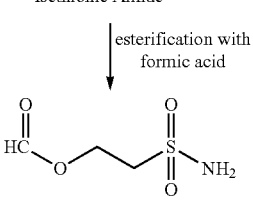

Chemical Formula: $C_2H_7NO_4S$
Molecular Weight: 153.16
2281A

In one embodiment, this disclosure includes a method of killing tumor stem cells by administering to a subject in need thereof a tumor stem cell killing effective amount of taurolidine, taurultam, or a mixture thereof. The tumor stem cell killing effective amount of taurolidine and/or taurultam is less than an amount of taurolidine and/or taurultam required for killing tumor cells.

In some embodiments, the taurolidine, taurultam, or a mixture thereof is administered in a tumor stem cell killing composition at a concentration of about 0.01 to about 500 µg/ml. In some embodiments, the taurolidine, taurultam, or a mixture thereof is administered in a tumor stem cell killing composition at a concentration of about 0.1 to about 100 µg/ml. In some embodiments, the taurolidine, taurultam, or a mixture thereof is administered in a tumor stem cell killing effective composition at a concentration of about 10 to about 50 µg/ml. Taurolidine is effective at killing tumor stem cells in tissue culture in vitro at 0.01 µg/ml.

In some embodiments, the taurolidine, taurultam, or a mixture thereof is administered in a tumor stem cell killing composition at a concentration of about 0.001 to about 2%. In some embodiments, the taurolidine, taurultam, or a mixture thereof is administered in a tumor stem cell killing composition at a concentration of about 0.01 to about 1.5%. In some embodiments, the taurolidine, taurultam, or a mixture thereof is administered in a tumor stem cell killing composition at a concentration of about 0.1% to about 1%.

In one embodiment, the taurolidine, taurultam, or a mixture thereof is administered for tumor stem cell killing to a subject in need thereof at a total daily dose of from about 0.01 g to about 50 g, about 0.1 g to about 30 g, about 0.5 g to about 10 g, or about 1 g to about 5 g.

Tumor stem cell killing effective dosage amounts of the taurolidine, taurultam, or a mixture thereof are dosage units within the range of about 0.01-500 mg/kg, preferably 1-100 mg/kg per day, and most preferably 5-50 mg/kg per day.

In another embodiment, this disclosure includes a method of killing tumor stem cells by administering to a subject in need thereof a compound selected from the following compounds:

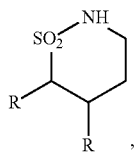

wherein each R is independently H, alkyl, or aryl,

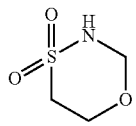
2250

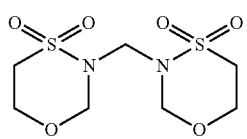
2245

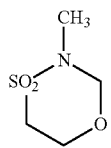
2255

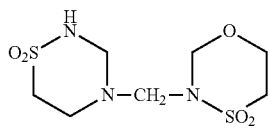
A1

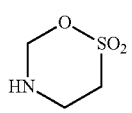
B1

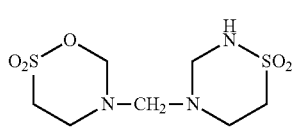
B2

-continued

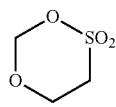
A3

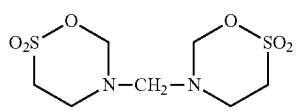
B3

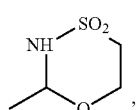
2256 which may be used in combination with taurolidine and/or taurultam. Such a technique provides a method for killing tumor stem cells using at least two compounds having different half-lives, and thereby broadening the pharmacokinetic effects obtained thereby. In one embodiment, compound 2250 may be used in combination with taurolidine and/or taurultam.

EXAMPLES

Example 1

Anti-Neoplastic Activity of Compound 2250

Introduction

Based on the recognition of taurolidine as a powerful anti-neoplastic agent, the analogue 2250 was synthesized by Geistlich Pharma.

Material and Methods

Chemicals: The compound 2250 and taurolidin 2% solution were provided by Geistlich Pharma AG, Wolhusen, assignee of the present invention.

Cell lines: The human glioma cell line LN-229 was used as described previously (Rodak et al. 2005) as well as the human colon adenocarcinoma cell line SW480.

Cytotoxicity assay: Dissociated LN-229 cells were seeded into 96-well plates at a density of $10^4$ cells per well in 100 µl of culture medium. Approximately 24 h later, when the cells had reached 70-80% confluency, the medium was changed and treatment with compound #2250 (4.0-1000 µg/ml), taurolidine (4.0-1000 µg/ml) or standard medium was started. Triplicate cultures were prepared for each sample. After 24 h of incubation at 25° C., the remaining adherent viable cells were stained using crystal violet as described (Rodack et al. 2005). Cell viability was determined by measuring the absorbency at 540 nm. The results are expressed as killing rate given by the difference between 100% of cells and percentage of cells surviving. $EC_{50}$ values correspond to the concentration inducing 50% cell death.

Results

Positive control: After incubating the human glioblastoma cells (LN-229) for 24 h with taurolidine, a concentration-dependent cytotoxicity was determined (Tab. 1, FIG. 1) with an $EC_{50}$=45 µg/ml, a value which corresponds to earlier results obtained with this cell line (Rodack et al. 2005).

Test of 2250: When 2250 was incubated under the same experimental conditions as taurolidine, a similar concentration-dependent loss of cell viability was observed. The half-maximal concentration of inducing cell death was $EC_{50}$=50 µg/µl (Tab. 1, FIG. 1).

Figure 2:
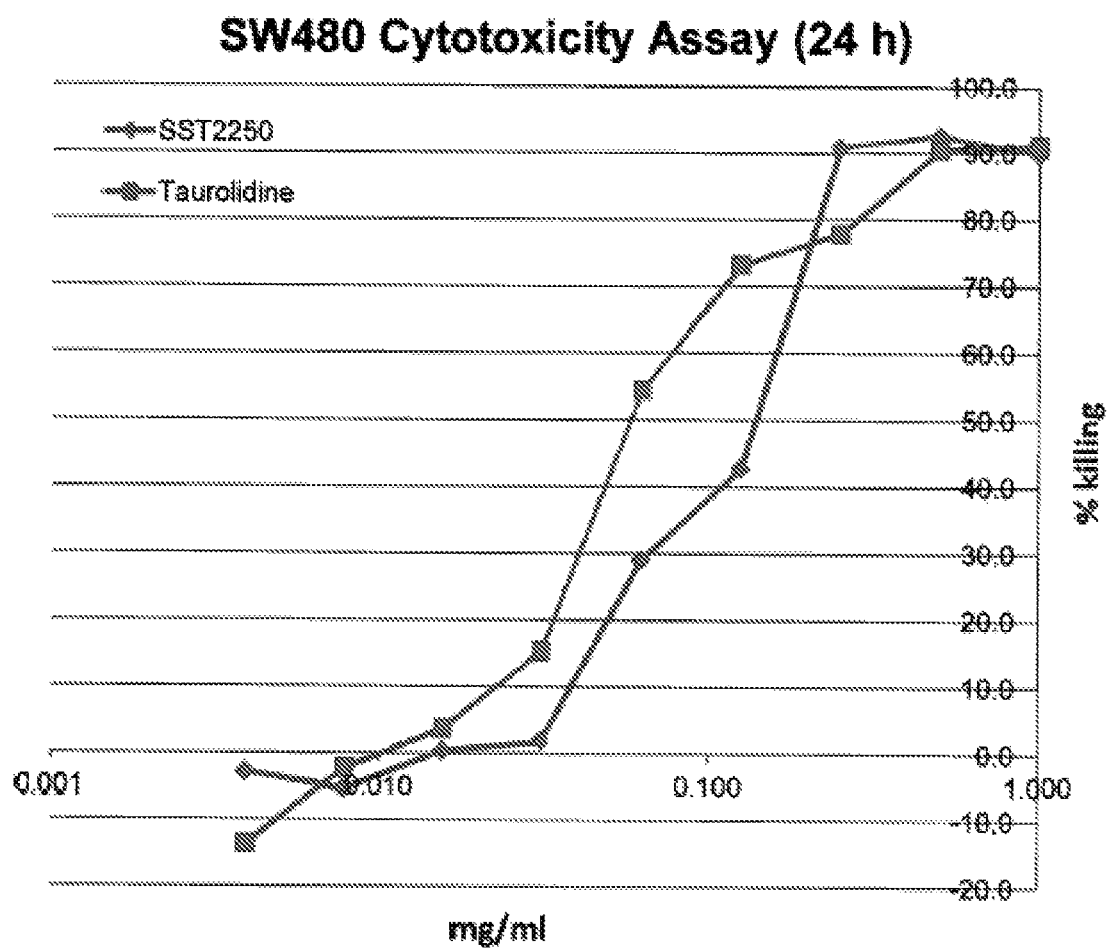
FIG. 2 graphically shows anti-neoplastic activity of one embodiment of the invention in a cytotoxicity assay in SW480 (human colon adenocarcinoma) cells.

The results for SW480 cell cytotoxicities are shown in FIG. 2.

Discussion

The compound 2250 represents a new avenue in the search for novel antineoplastic agents of the taurolidine-type. Biologically, the compound is as potent as taurolidine. Chemically, the compound shows strikingly different features from taurolidine. By replacing a NH group by an ether-oxygen, the double ring structure of taurolidine is avoided. Compound 2250 is a single ring structure and a close structural analogue of taurultam.

Mechanistically, the results show that the antineoplastic activity of taurolidine is unlikely to be due to the formation of a methoxy-derivative, since 2250 is devoid of a methoxy group. The compound causes blebbing of tumor cells.

Summary

The compound 2250 shows potent antineoplastic activity in vitro, as determined for human glioblastoma cells (cell line LN-229). Its potency ($EC_{50}$=45 µg/ml) is comparable to that of taurolidine ($EC_{50}$=50 µg/ml) as tested in the same cell line.

TABLE 1

Cytotoxicity of 2250 and taurolidine against LL-229 glioblastoma cells.

| Concentration µg/ml | 1000 | 500 | 250 | 125 | 62.5 | 31 | 15.5 | 8 | 4 | — |
|---|---|---|---|---|---|---|---|---|---|---|
| Taurolidine OD ± SD | 0.109 ± 0.010 | 0.098 ± 0.007 | 0.165 ± 0.002 | 0.305 ± 0.008 | 0.317 ± 0.008 | 1.132 ± 0.042 | 1.434 ± 0.031 | 1.478 ± 0.040 | 1.530 ± 0.026 | 1.435 ± 0.009 |
| Comp. 2250 OD ± SD | 0.189 ± 0.007 | 0.141 ± 0.007 | 0.120 ± 0.012 | 0.199 ± 0.014 | 0.372 ± 0.006 | 1.482 ± 0.099 | 1.482 ± 0.029 | 1.527 ± 0.033 | 1.477 ± 0.069 | 1.483 ± 0.013 |

The values were measured in triplicate and the OD is the absorbance at 540 nm plus minus standard deviation (SD). High values correspond to high cell viability.

Example 2

The new compound 2250 (Tetrahydro1,4,5-oxathizain-4-dioxid) was tested and found to have a very high level of antibacterial activity against *Staphylococcus aureus* and *Escherichia coli*. The antibacterial activity against *Staph. aureus* is about double as high as Taurultam.

Example 3

In punch plate tests, Compound 2250 was tested and found highly active against MRSA lines 188, 189, 193, 194 and 195.

By displaying a combination of antimicrobial and antineoplastic activity, compound 2250 is particularly suitable for surgical oncology.

Example 4

Each of compounds identified herein as compound 2250, 2255, 2245, A1, A3, B1, B2, or B3 is tested against cancer cell lines of cancers identified herein, and found to be active against such cell lines.

Example 5

Each of compounds identified herein as compound 2250, 2255, 2245, A1, A3, B1, B2, or B3 is administered to patients having cancers identified herein, and is found to be effective in treating such cancers and safe for use in patients.

Each of these compounds is administered with Vitamin D3, a derivative, metabolite or analog thereof and the combination is found to increase the anti-tumor effects of the compounds.

Example 6

The half-life of compound 2250 in human fresh blood was measured at 37° C. in vitro by GC, PYE Unicam Series 204 FID.
Baseline Value: 49.0 ppm
After 1 hour: 50.6 ppm
After 2 hours: 47.6 ppm
After 20 hours: 38.6-39.0 ppm.

Thus, the half-life of compound 2250 is greater than 24 hours in human blood, which is significantly higher than the half-life of taurolidine, which was found to be ~30 minutes using the same test.

Example 7

Tissue samples from high grade gliomas WHO grade IV from newly diagnosed patients (medium age of 54±10 years) were minced mechanically, digested enzymatically and the dissociated cells were filtered. The isolated tumor cells were cultured as bulk cells. Cancer Stem Cells (CSCs) were isolated by the formation of neurospheres under neurosphere conditions (using neurobasal medium) from the murine SMA 560 glioma cell line or from freshly isolated human glioblastoma cells.

Cytotoxicity Assay

Figure 3A:
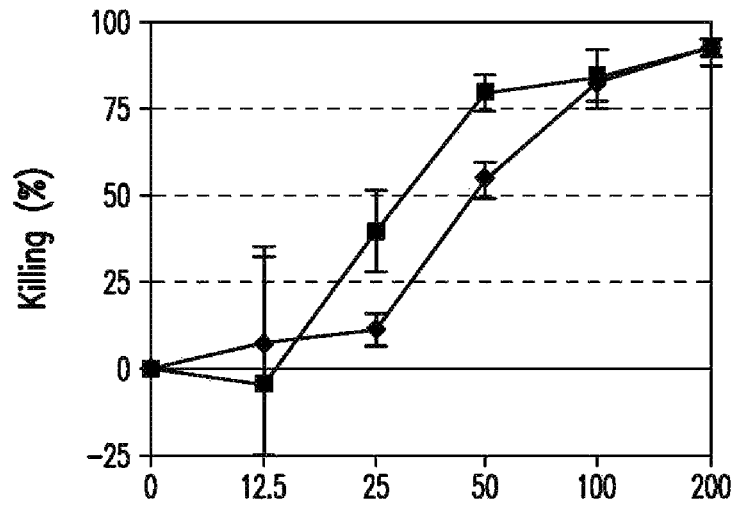
FIG. 3A-3C Cytotoxicity induced in murine SMA 560 bulk glioma cells after treatment with taurolidine and taurultam (TT). Cytotoxicity was assessed after 24 h (FIG. 3A) and 48 h (FIG. 3B) of treatment. The $EC_{50}$ values for taurolidine (34.6 µg/ml) and taurultam (19.3 µg/ml) are given in the lower panel (FIG. 3C). Data are presented as mean values±SD of three independent experiments.
Figure 3B:
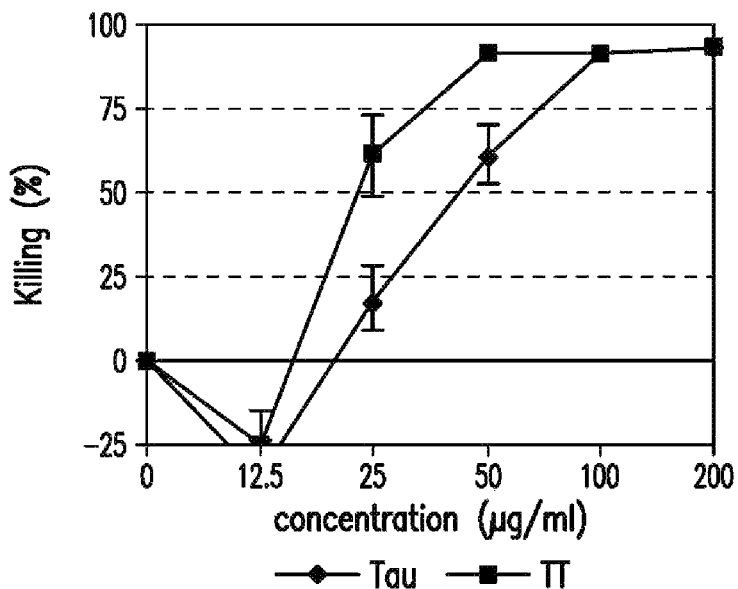
Figure 3C:
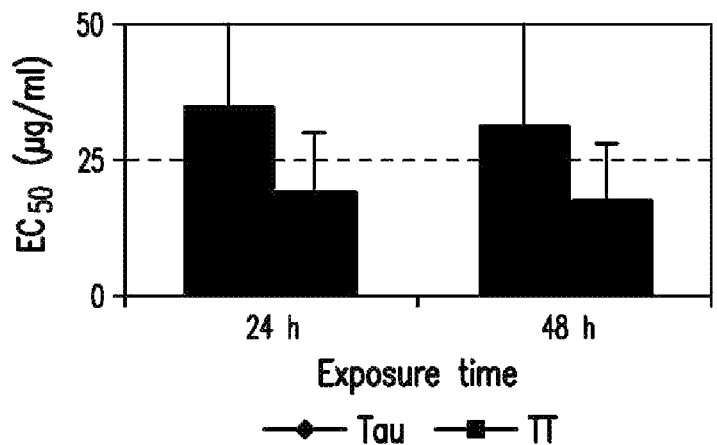

Bulk glioma tumor cells were cultured and incubated with taurolidine or taurultam for 24 h or 48 h as described previously (Rodak et al., J. Neurosurg. 102, 1055-1068, 2005). CSCs were cultured for 7 days and subsequently exposed to taurolidine, taurultam or temozolamide for 24 hours. The number of remaining adherent cells were stained (crystal violet or Alamar Blue) and quantified by absorbance measurements (540 nm). Cell survival was expressed as the percentage of cells surviving relative to the number of cells surviving in untreated control cultures. The results are given as % killing rate or $EC_{50}$ as the dose required for half-maximal cytotoxicity. Results Cytotoxicity of Taurolidine and Taurultam Against Cancer Cells and Cancer Stem Cells From the Mouse The mouse SMA560 glioma cell line was used to provide tumor bulk cells and CSCs. Following incubation of SMA560 bulk cells with various concentrations of taurolidine and taurultam (6.25, 12.5, 25, 50, 100, 200 µg/ml), cytotoxicity was determined after 24 h and 48 h of incubation. For both taurolidine and taurultam, a clear dose-dependent cytotoxicity was found with no major difference in potency between the 24 h and 48 h time of incubation (FIG. 3A,B). The $EC_{50}$ value was 34.6 µg/ml for taurolidine and 19.3 µg/ml for taurultam (FIG. 3C).

Figure 4:
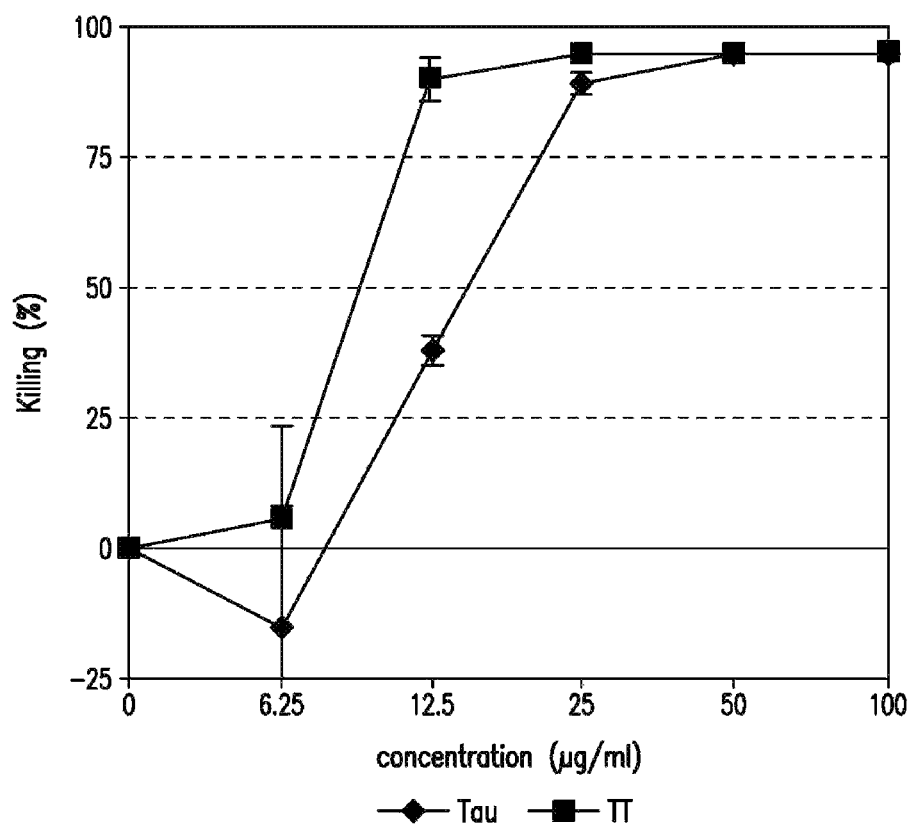
FIG. 4 Cytotoxicity induced by taurolidine and taurultam (TT) in murine SMA560 glioma cancer stem cells (CSC). Data are presented as mean values±SD.

Mouse CSCs were generated from the SMA560 glioma cell line and cultured for 7 days. The CSCs were treated with the same concentration of taurolidine and taurultam as above and cytotoxicity was determined after 24 hours. As shown in FIG. 4, both taurolidine and taurultam showed a dose dependent cytotoxicity with an $EC_{50}$ of 12.5 μg/ml for taurolidine and $EC_{50}$ of 10 μg/ml for taurultam against murine CSCs. These values demonstrate for the first time that taurolidine and taurultam are effective against a CSC. Taurolidine and Taurultam Induce Cell Death in Human CSC Isolated From Four Different Glioblastoma Patients.

Figure 5A:
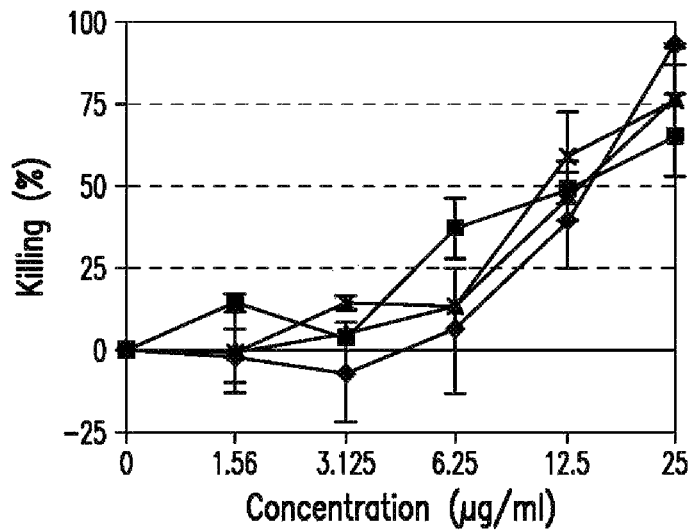
FIG. 5A-5C Cytotoxicity induced in cancer stem cells isolated from four glioblastoma multiforme (GBM) patients (GBM #3, #4, #5 and #6) after treatment for 24 h with taurolidine (FIG. 5A), taurultam (TT) (FIG. 5B) or temozolamide (FIG. 5C). Data are presented as mean values±SD.
Figure 5B:
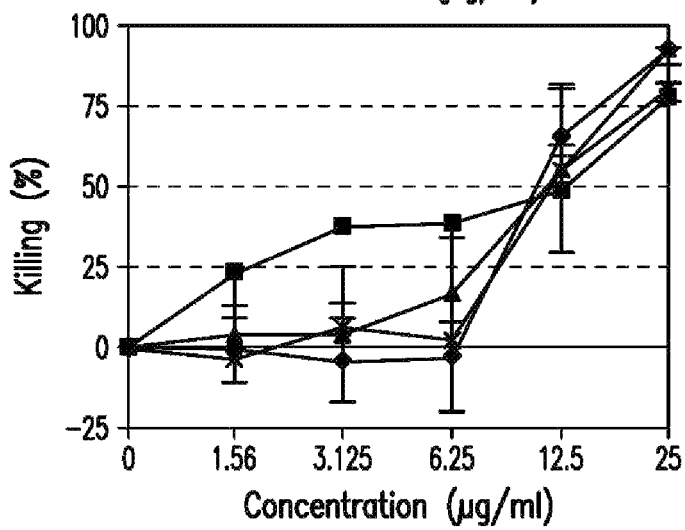
Figure 5C:
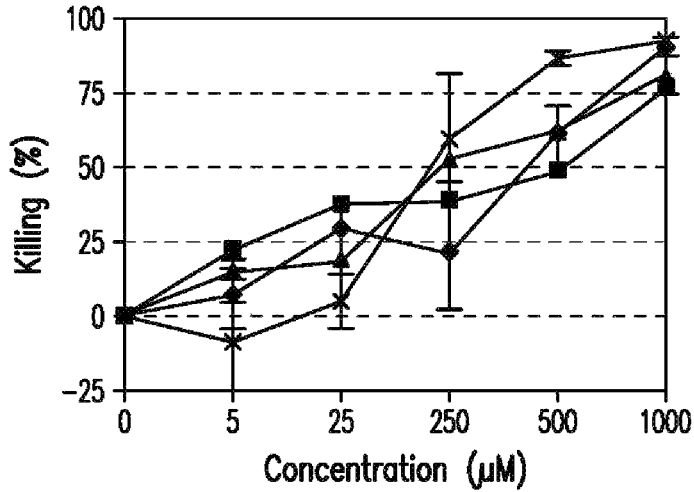
Figure 6:
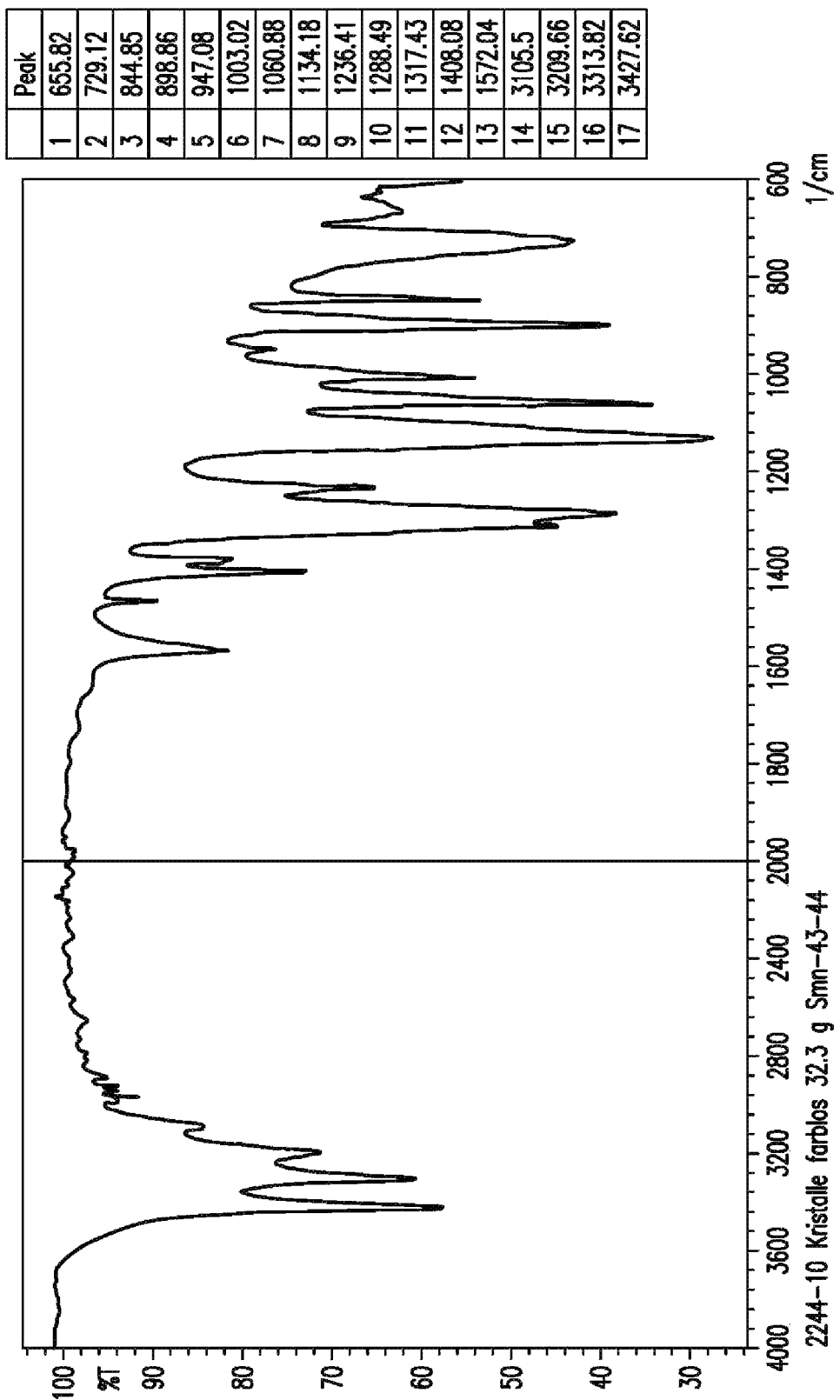
FIG. 6 FTIR spectrum of compound 2244 made according to the present invention.

CSCs were isolated from glioblastoma tissue resected from four patients. The same range of concentrations of taurolidine and taurultam was applied as above and the cytotoxicity was measured after 24 hours of incubation with drug. All four glioblastoma CSCs tested (GBM #3, #4, #5 and #6) were similarly sensitive to taurolidine and taurultam (FIG. 5A,B). The mean $EC_{50}$ value of taurolidine was 13±2 μg/ml, the $EC_{50}$ value of taurultam was 11±1.4 μg/ml (Table 2). In these experiments, the cytotoxic capacity of taurolidine and taurultam was compared with that of temozolamide (TIM) applied in the concentration range of 5 μM to 1,000 μM (FIG. 2C). The mean $EC_{50}$ value of TMZ was 68.5±26 μg/ml (Table 2). Interestingly, this concentration is much higher than peak plasma levels of TMZ measured in patients (13.7 μg/ml) (Portnow et al., Clin Cancer Res 15, 7092-7098, 2009).

The results demonstrate that both taurolidine and taurultam are effective against CSCs and this finding was established for glioma CSCs from two species, mouse and man.

The mouse CSCs were generated from a mouse glioma cell line (SMA 560). Remarkably, based on the $EC_{50}$ values, the CSCs were even more sensitive to taurolidine and taurultam than the corresponding glioma bulk cells (about 3 fold for taurolidine and 2 fold for taurultam) (FIGS. 3, 4).

Human CSCs, freshly isolated from four human glioblastoma patients, were likewise highly chemosensitive to both taurolidine and taurultam. The $EC_{50}$ values for cytotoxicity were 13±2 ug/ml and 11±1.4 μg/ml, respectively (Table 2). These values demonstrate that the human CSCs, like their murine counterparts, are more sensitive to taurolidine and taurultam (about 3 to 4 fold) than the human glioblastoma bulk cells which display $EC_{50}$ values in the range of 50 μg/ml (Rodak et al., J. Neurosurg., 102, 1055-68, 2005).

TABLE 2

Cytotoxicity Induced by taurolidine (Tau), taurultam (TT) or temozolamide (TMZ) in cancer stem cells (CSC) derived from four glioblastoma patients. $EC_{50}$ (μg/ml) = drug concentration resulting in 50% cell death compared to untreated control cultures in vitro.

| Cancer Stem Cells | n | Cytotoxicity EC50 (μg/ml) 24 h | | |
|---|---|---|---|---|
| | | Taurolidine | Taurultam | Temozolamide |
| GBM #3 | 3 | 15 | 10.5 | 84.4 (435 μM) |
| GBM #4 | 2 | 12.5 | 12.5 | 97 (500 μM) |
| GBM #5 | 2 | 14 | 11 | 48.5 (250 μM) |
| GBM #6 | 3 | 10 | 9 | 44 (230 μM) |
| Mean ± SD | | 13 ± 2 | 11 ± 1.4 | 68.5 ± 26 |

Example 8

Taurolidine and taurultam were tested against cancer stem cells derived from a murine glioma cell line and human cancer stem cells. Taurolidine and taurultam were found to exert potent anti-neoplastic activity against cancer stem cells derived from a murine glioma cell line ($EC_{50}$=12.5 μg/ml for taurolidine, $EC_{50}$=10 μg/ml for taurultam) as well as against human cancer stem cells, freshly isolated from four glioblastoma patients ($EC_{50}$=13±2 μg/ml for taurolidine; $EC_{50}$=11±1.4 μg/ml for taurultam).

Example 9

Antineoplastic Effect on Pancreatic Stem Cell-Like Multicellular Spheroid Cultures.

Multicellular spheroids are composed of tumor cells growing in a 3-dimensional structure stimulating the growth, micro-environmental conditions and stem cell-like characteristics of real tumors. The multicellular tumor spheroid (MCTS) model compensates for many of the deficiencies seen in monolayer cultures. Spheroids on the scale of 200-500 μm develop chemical gradients of oxygen, nutrients, and catabolites, while having morphological and functional features similar to tumors. Therefore, assays utilizing the MCTS model allow for the assessment of drug penetration and are more predictive of in vivo success compared with monolayer cultures. MCTS assays are a tumor model system of intermediate complexity between standard monolayer and tumors in vivo.

Pancreatic tumor cells (Panc Tu-1, BxPC-3, Mia Paca-2, ASPC1) and pancreatic primary tumor cells (Bo80) were seeded in ultra-low adhesion plates in special stem cell media.

Pancreatic tumor cells (ASPC1, Mia Paca-2, Panc Tu1, BxPC-3) and pancreatic primary tumor cells (Bo80) were raised in monolayer culture before seeding in ultra low adhesion plates under conditions of special stem cell media to form multicellular spheroids and passed through a cell strainer to exclude aggregates.

Half-maximal inhibition of cell viability was achieved with 750-1000 μM of compound 2250 in tumor cell lines AsPC-1, BxPC-3 and HCT-116. These effects are similar to those observed in glioma cell line LN-229. The induction of cell death was due to apoptosis and necrosis (most likely necroptosis). It was found that the induction of this programmed cell death was prevented by addition of the reducing agent N-acetylcysteine and that caspases are not involved. Thus, there is a redox-directed mechanism of action.

The growth of pancreas tumor cells (AsPC-1, BxPC-3 and HCT-116) was inhibited by compound 2250 with a half-maximal concentration of 300 μM, which is considerably lower than the concentration needed to elicit cytotoxicity.

As shown in FIG. 8, multicellular pancreatic tumor (Panc Tu1 or BxPC-3) spheroids were tested as control, taurolidine-treated (500 μM) or compound 2250-treated (1000 μM) samples for 48 hours (columns labeled A). After treatment, each of the whole cell suspensions was passed through a 45 μm cell strainer again to analyze residual aggregates for their stability (columns labeled B).

Figure 9A:
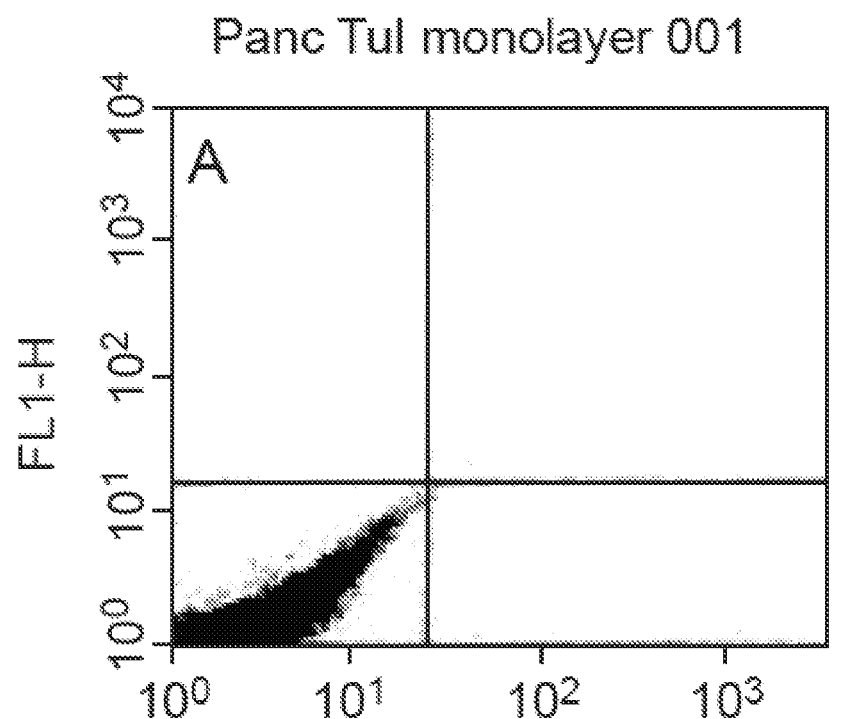
FIGS. 9A and 9B show the results of FACS analysis of the Panc Tul multicellular spheroid cultures CD133 content.
Figure 9B:
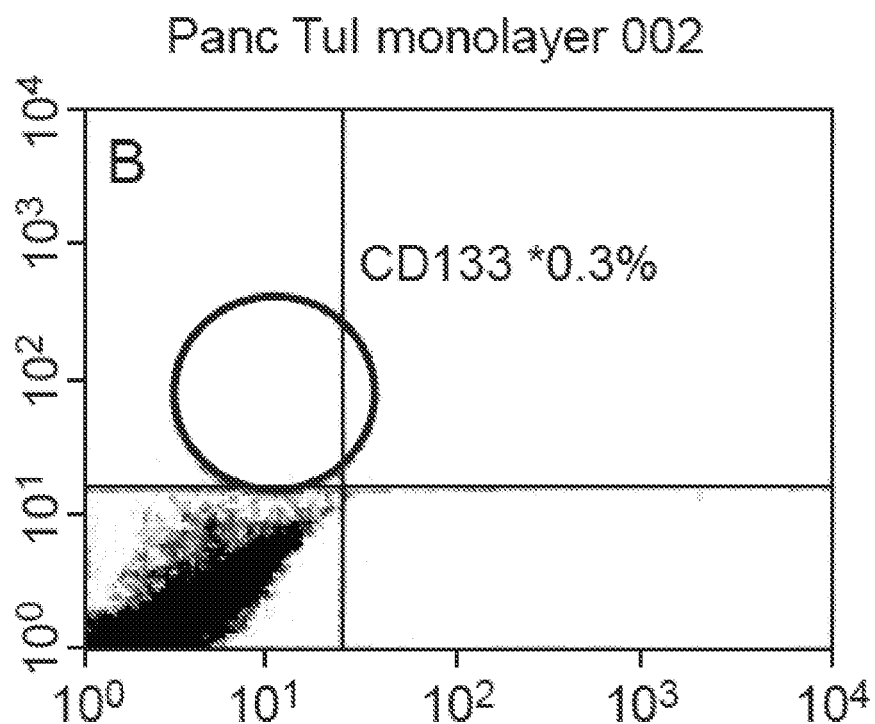

FIGS. 9A and 9B show the results of FACS analysis of the Panc Tu1 multicellular spheroid cultures CD133 content. CD133 is a known and well-established hallmark of stem cells. The results show that the amount of CD133-positive cells in multicellular spheroid cultures of Panc Tu1 was enriched 10-fold compared to Panc Tu1 grown in monolayer culture (B). Isotype IgG was used as negative control (A). The results demonstrate that taurolidine and compound 2250 have an antineoplastic effect on the pancreatic stem cell like multicellular spheroid cultures.

Example 10

In vivo study of taurolidine and compound 2250 as antineoplastic agents in malignant pancreatic carcinoma.

The effects of taurolidine and compound 2250 were analyzed on nude mice (NMRI-Foxn1 nu/nu). 1×10$^7$ tumor cells (PancTu-I and MiaPaca 2) were injected subcutaneously into the flank. The animals were randomized into three groups: the control group; the group treated i.p. with taurolidine (TRD), and the group treated i.p. with compound 2250 (NDTRLT).

Tumors were grown to a size of 200 mm$^3$ before the treatment was started. Mice were treated on alternating days with 500 mg/kg*body weight (BW).

Figure 10A:
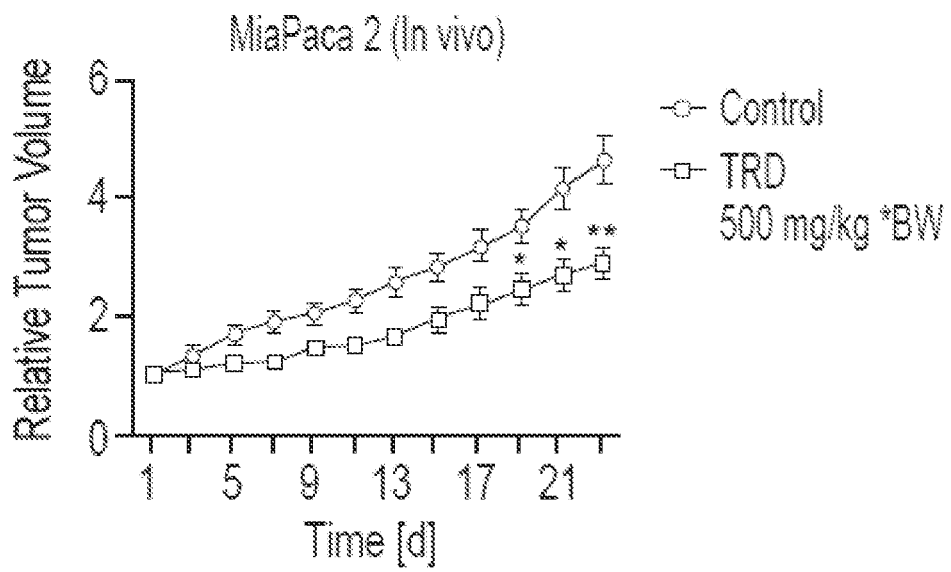
FIG. 10A shows MiaPaca2 tumor volume upon treatment with control or taurolidine.

As shown in FIG. 10A, administration of taurolidine decreased MiaPaca2 tumor volume significantly compared to control (by about 2-fold).

Figure 10B:
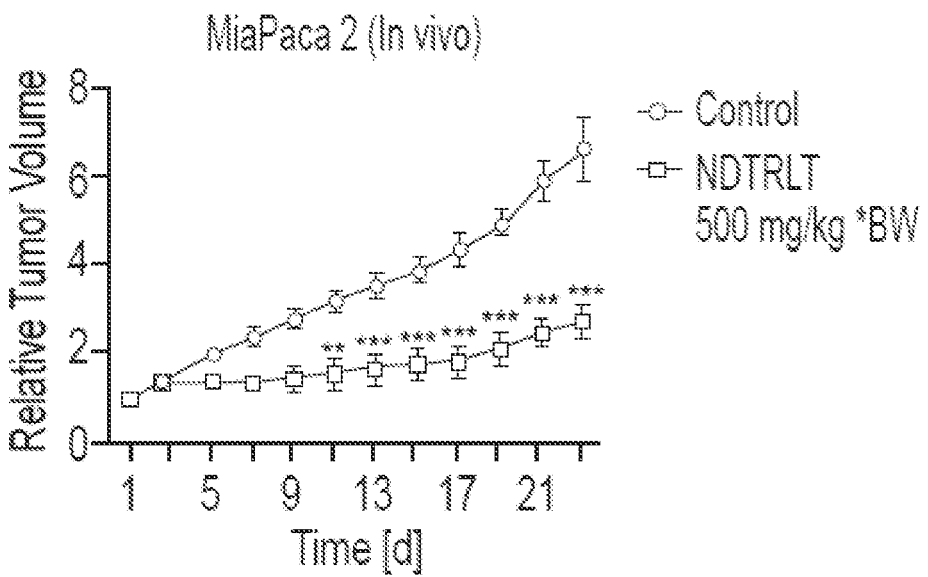
FIG. 10B shows MiaPaca2 tumor volume upon treatment with control or compound 2250.

As shown in FIG. 10B, administration of compound 2250 decreased MiaPaca2 tumor volume significantly compared to control (by over 3-fold).

Figure 10C:
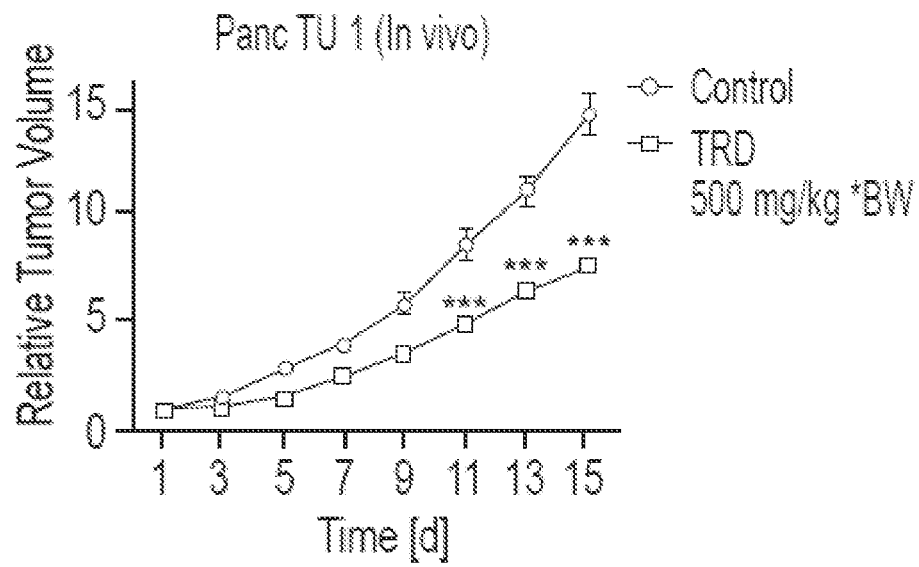
FIG. 10C shows PancTu I tumor volume upon treatment with control or taurolidine.

As shown in FIG. 10C, administration of taurolidine decreased PancTu I tumor volume significantly compared to control (by about 3-fold).

Figure 10D:
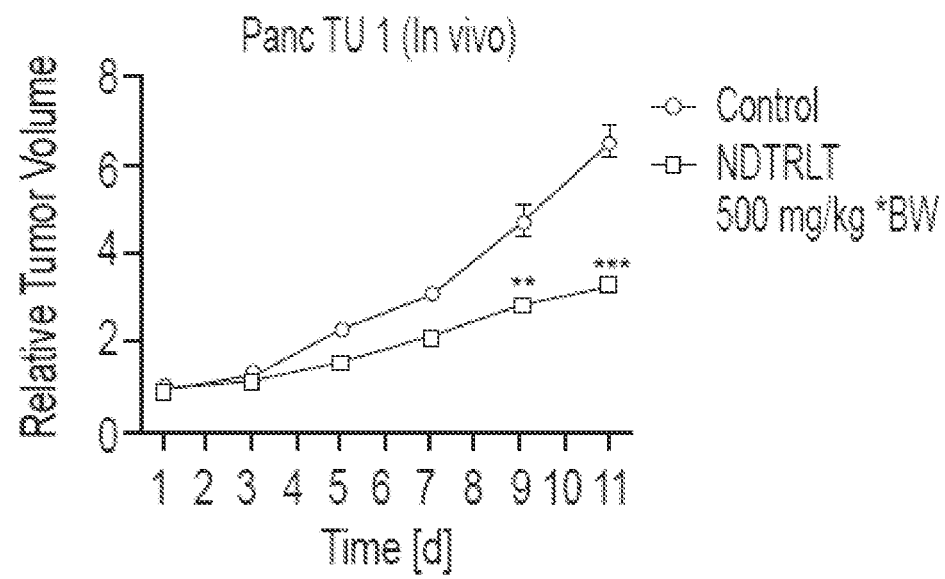
FIG. 10D shows PancTu I tumor volume upon treatment with control or compound 2250.

As shown in FIG. 10D, administration of compound 2250 decreased PancTu I tumor volume significantly compared to control (by about 2-fold).

The applied taurolidine and compound 2250 dosages showed no toxic effect on the mice during the study. In both tumor cell line models, a significant reduction of tumor growth was obtained.

Tumor growth (volume) was significantly reduced from day 9 onwards (PancTuI) and day 11 onwards (MiaPaca2) versus controls. The dose of 500 mg/kg i.p. was well tolerated with no overt sign of toxicity.

Figure 11A:
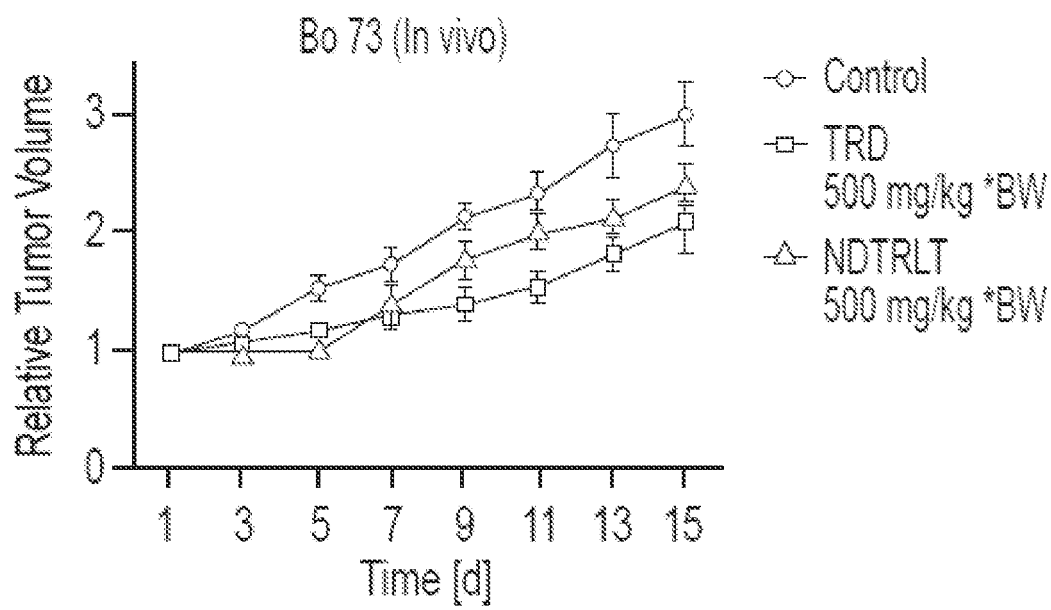
FIG. 11A is a xenograft model of pancreatic primary tumors (Bo 73) observed for 15 days when treated with control, taurolidine or compound 2250.
Figure 11B:
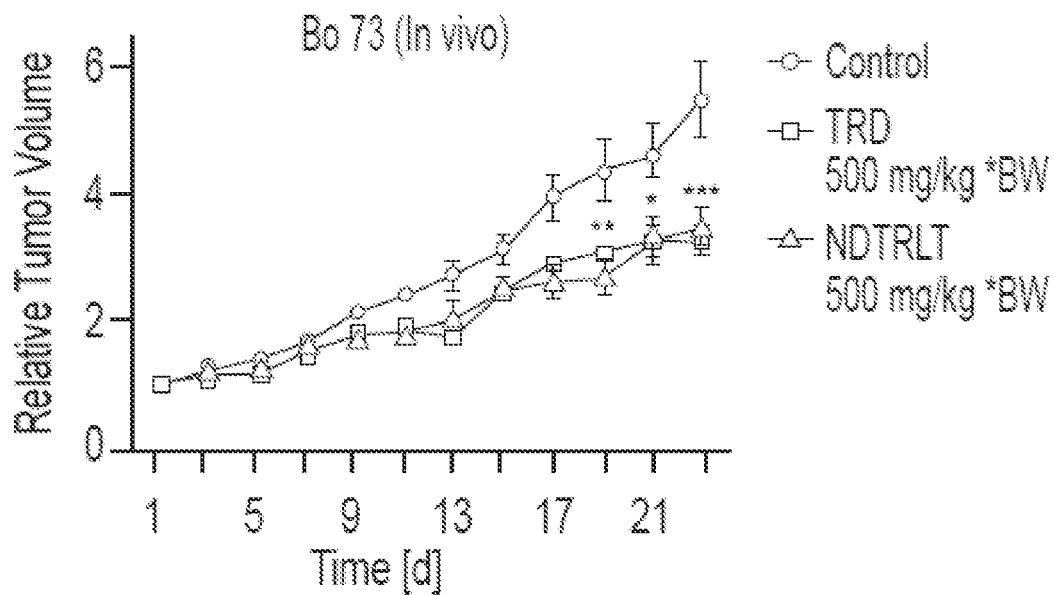
FIG. 11B is a xenograft model of pancreatic primary tumors (Bo 70) observed for 23 days when treated with control, taurolidine or compound 2250.

As shown in FIG. 11A, a xenograft model of pancreatic primary tumors (Bo 73) was observed for 15 days and it was found that administration of taurolidine slightly reduced relative tumor volume compared to control and administration of compound 2250 further reduced relative tumor volume compared to control. However, the differences in tumor volumes were not statistically relevant, likely due to the short duration of the study and the slow growth rate of the tumors. In FIG. 11B, a xenograft model of pancreatic primary tumors (Bo 70) was observed for 23 days and it was observed that administration of taurolidine and compound 2250 significantly reduce tumor volume compared to control.

Administration, e.g., intraperitoneally, of taurolidine and/ or compound 2250 inhibits tumor growth in vivo.

Example 11

Cell Lines and Culture Methods

For all assays two cSCC cell lines were used, namely SCC13 and A431. SCC13 are human, epidermal, tumorigenic, p16- and p53-deficient squamous carcinoma cells. A431 are epidermoid, tumorigenic, p53-deficient squamous carcinoma cells, showing high EGFR expression.

The cSCC cell lines A431 and SCC13 cells were cultured in Dulbecco's Modified Eagle Medium (DMEM), supplemented with the antibiotics penicillin (100 U/ml), streptomycin (100 U/ml) and 2 mM L-Glutamine. Cells were grown in cell culture dishes (diameter 100 mm, surface 60 cm$^2$) in humidified 5% CO2 atmosphere at 37° C. and grown as monolayer for at least 72 h.

Dose Finding Trials and Cell Characteristics

The different cell lines were incubated in a sub-confluent state with different concentrations of the substance, compared to an untreated control for 6, 12, 24 and 48 hours, in order to determine the dose-effect-relation and to establish the most effective single concentration. Dose finding trials were performed using the MTT cytotoxicity assay, as described here below.

SCC13 are rapidly growing cSCC cells, which show a high proliferation rate. The most effective concentrations for all carried out SCC13 assays were for substance GP-2250 increasing dosages of 100, 150, 200, 300, 400 μmol/l. The A431 cells are slower proliferating cells than SCC13 cells. The most effective concentrations for all carried out A431 assays were therefor increasing dosages of 50, 100, 125, 150, 200 μmol/l.

MTT Assay

In order to analyze and quantify the anti-neoplastic effect of substance GP-2250 on cell viability and to determine its dose-response effect, colorimetric MTT assays were performed with both cell lines.

Cells were seeded to a density of 5×10$^3$ cells/well in 96-well plates and incubated for 24 hours in order to obtain a sub-confluent monolayer. The medium was then removed and cells were incubated for 6, 12, 24 and 48 hours with new medium (100 μl/well) containing increasing concentrations of substance GP-2250 and ddH2O as negative control. The most effective dose-responses for SCC13 cells were 100, 150, 200, 300, 400 μmol/l of substance GP-2250 and for A431 cells 50, 100, 125, 150, 200 μmol/l. Two hours before measurement, the yellow coloured MTT reagent 3-(4,5-dimethylthiazol-2-yl)-2,5-diphenyl tetrazolium bromide (5 mg/ml) was administrated. It is reduced through mitochondrial dehydrogenase of metabolic viable cells into violet coloured formazan crystals, which can be measured by photometry. The test media were removed and 100μl DMSO (Dimethyl sulfoxide) was applied. After an incubation time of 10 min the viability of cells was analysed by using a microplate absorbance reader (ASYS, UVM340, Anthos Mikrosystheme GmbH, Germany), measuring the optical density. The amount of violet formazan crystals is directly proportional to the amount of viable cells. (25) For every cell line six independent assays were performed with consecutive cell passages.

BrdU Proliferation Assay, ELISA

In order to analyse and quantify the anti-proliferative effect of substance GP-2250, BrdU (5-bromo-2-deoxyuridine) proliferation assays, ELISA (Roche Applied Science, Mannheim, Germany), were performed with all cell lines, according to the manufacturer's instructions (Version 16, content version: January 2013, Cat. No. 11 647 229 001). This proliferation assay is a non-isotopic colorimetric immunoassay for quantification of BrdU incorporation into newly synthesised DNA of actively proliferating cells.

Cells were seeded to a density of 8×10$^3$ cells/well in 96-well plates and incubated for 24 hours in order to obtain a sub-confluent monolayer. The medium was then removed and cells were incubated for 6 hours and 24 hours with new medium (100 μl/well) containing increasing separate concentrations of substance GP-2250 and ddH2O as negative control. The most effective dose-responses for SCC13 cells were 100, 150, 200, 300, 400 μmol/l and for A431 cells 50, 100, 125, 150, 200 μmol/l. After the 6- or 24-hours incubation period the BrdU reagent was added for additional 2 hours, before cells were introduced to the BrdU proliferation assay (Roche Applied Science, Mannheim, Germany), as described by the manufacturer's instructions. BrdU is a nucleoside analogue of (3H)-thymidine, which is incorporated into new strands of synthesised chromosomal DNA during the S-phase of the cell cycle. The amount of cell proliferation was detected and measured via optical density, using a microplate absorbance reader (ASYS, UVM340, Anthos Mikrosystheme GmbH, Germany). All BrdU assays were performed with eight replicates of three independent experiments with consecutive passages. The incubation time of 6 hours has been shown to be the most appropriate for the BrdU proliferation assays.

Flow Cytometry (FCM)

Cells were seeded to a density of $2\times10^5$ cells/well in 6-well plates and incubated for 24 hours in order to obtain a sub-confluent monolayer. The medium was then removed and cells were incubated for 24 and 48 hours with new medium containing increasing separate concentrations of substance GP-2250 and ddH2O as negative control. The most effective dose-responses for SCC13 cells were 100, 150, 200, 300, 400 µmol/l and for A431 cells 50, 100, 125, 150, 200 µmol/l.

Cell numbers were determined individually from each dose-dependent suspension, then fixed in 200 µl binding buffer (Bender MedSystems, Vienna, Austria) and 5 µl Annexin V-FITC (BD Biosciences, Heidelberg, Germany) was added. After 15 minutes incubation at room temperature and light deprivation 10 µl Propidium iodide (PI) (Bender MedSystems, Vienna, Austria) was added. Cells were immediately analysed for Annexin V-FITC and PI binding using a flow cytometer (FACS Calibur BD Biosciences, Heidelberg, Germany) and quantified through dot plots histograms analysed by CellQuest Pro software (BD Biosciences, Heidelberg, Germany). Viability was defined by Annexin V-FITC and PI negative, apoptosis by Annexin V-FITC positive and PI negative and necrosis by Annexin V-FITC negative and PI positive cells.

Statistical Analysis

The data of the anti-neoplastic effects of all MTT assays (percentage of viable cells), BrdU proliferation assays (percentage of proliferating cells) and FCM-analysis (percentage of viable, apoptotic and necrotic cells) was statistically analysed with the data processing GraphPad Prism software (version 8.0). The results are expressed as mean value (%) and its standard deviation (±SD %). For the statistical comparison between the experimental groups, considering normal distribution, a one-way ANOVA was performed, followed by a Turkey's post-hoc test. P-value less than 0.05 was considered statistically significant. Significance levels were categorised and indicated in the figures as follows: *p≤0.05, p≤0.01, *p≤0.001 and n.s.=not significant.

Substance GP-2250 Showed a Significant Cytotoxic Effect on Both cSCC Cell Lines

Figure 12B:
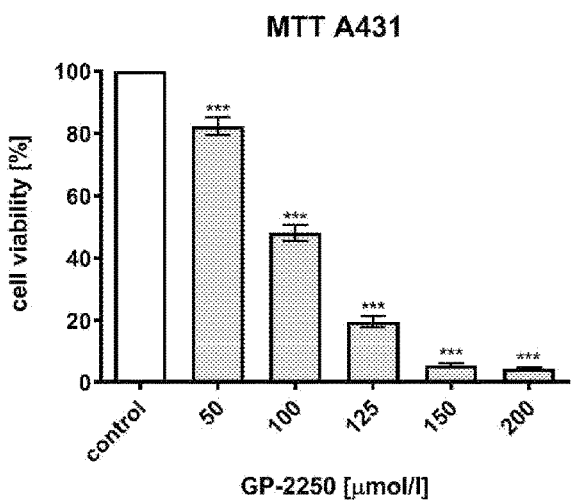

MTT assays were conducted with SCC13 and A431 cell lines in order to analyse the effects of substance GP-2250 on cell viability. As indicated in FIG. 12A-12B, both cell lines have been incubated for 24 hours with different increasing concentrations of GP-2250: SCC13 cells were separately incubated with 100, 150, 200, 300 and 400 µmol/l; A431 cells with 50, 100, 125, 150 and 200 µmol/l. Controls were set to 100% and defined as baseline.

Compared to untreated controls (ddH2O), GP-2250 leads to a significant dose dependent reduction of cell viability, as revealed by optical density measurement. The greater the concentration, the greater the cytotoxic effect of GP-2250 in both cell lines. Viability reduction of 50% or greater compared to the untreated control (100%) was obtained for SCC13 cells with a concentration of 150 µmol/l GP-2250 showing 42.74% (±1.43%) cell viability and for A431 cells with a concentration of 100 µmol/l showing 48.13% (±2.51%) (p<0.001) cell viability.

The maximum dose of GP-2250 led to an intense cytotoxic effect in all cell lines, leading with a concentration of 400 µmol/l in SCC13 cells to a viability of 9.09% (±0.85%) and respectively with a concentration of 200 µmol/l in A431 cells to 4.20% (±0.47%) cell viability (Table 2). Even though concentrations were different in both cell lines, the dose-effect of each substance on viable cells were comparable and proportional in both MTT groups.

The $IC_{50}$ value was determined by the dose of GP-2250 which caused a 50% reduction in cell numbers compared to controls. The $IC_{50}$ for GP-2250 varied between the two cell lines. $IC_{50}$ was obtained in SCC13 cells with a concentration of 190 µmol/l for substance GP-2250 and in A431 cells with concentrations of 96 µmol/l respectively.

Substance GP-2250 Significantly Inhibited Proliferation in all cSCC Cell Lines

Figure 13A:
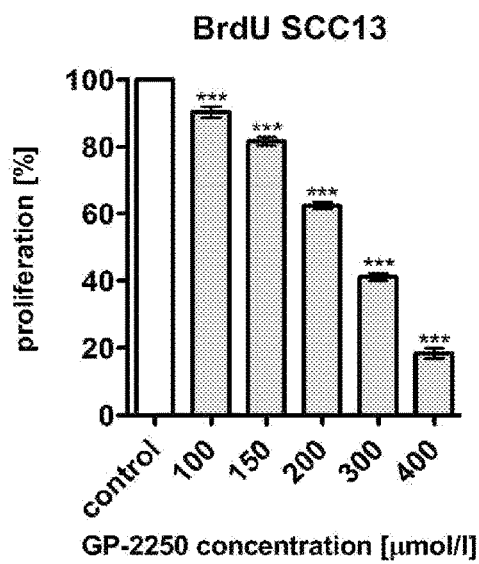
FIGS. 13A and 13B show the effects of GP-2250 in different cSCC cell lines, measured by BrdU assay.
Figure 13B:
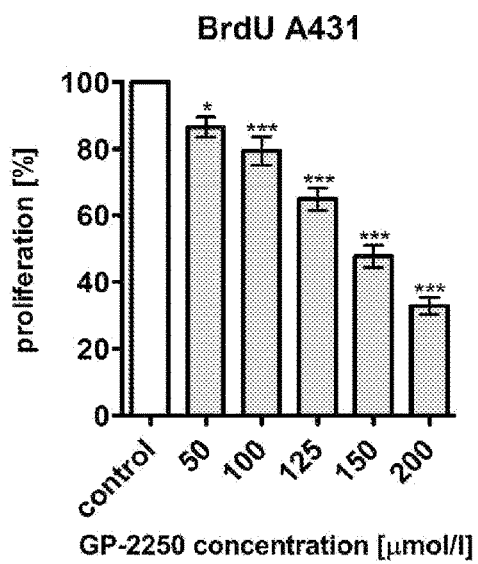

BrdU assays were conducted with both cSCC cell lines in order to analyse the effects of substance GP-2250 on cell proliferation. As depicted in FIG. 13A-13B, both cell lines have been incubated for 6 hours with different increasing concentrations of GP-2250: SCC13 cells were incubated with 100, 150, 200, 300 and 400 µmol/l; A431 cells with 50, 100, 125, 150 and 200 µmol/l. Controls were set to 100% and defined as baseline.

Compared to untreated controls (ddH2O), GP-2250 lead to a significant dose-dependent reduction of cell proliferation, as revealed by optical density measurement. Lowest dosages of GP-2250 showed already a significant reduction of proliferated cells compared to the untreated control (FIGS. 13A-13B). The greater the concentration, the fewer the amount of proliferating cells. The highest dosages of GP-2250 showed a highly significant reduction of proliferated cells of more than 75% compared to the control in SCC13 cells, leading for a dosage of 400 µmol to 18.41% (±1.50%); a dosage of 200 µmol lead to 32.85% (±2.52) of proliferation in A431 cells. The dose related effect of substance GP-2250 can be characterized as comparable and proportional in both cSCC cell lines.

Substance GP-2250 Significantly Induces Apoptotic Cell Death in Both cSCC Cell Lines FCM analysis was conducted to evaluate the impact of substance GP-2250 on inducing apoptosis. SCC13 and A431 cells have been incubated for 24 hours with substance GP-2250 in different concentrations, as summarized in FIGS. 14A-14F, and evaluated by FCM analysis, resulting in a significant viable cell reduction and increase of apoptotic and necrotic cells in comparison to controls (with ddH2O).

Figure 14A:
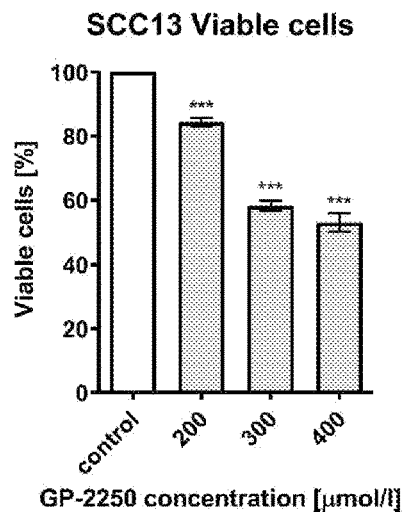
FIGS. 14A-14F show the effects of GP-2250 in different cSCC cell lines, measured by FCM analysis. SCC13 cells were incubated with GP-2250 (200, 300 and 400 µmol/l) and A431 cells were incubated with GP-2250 (100, 150 and 200 µmol/l), both for 24 h. The percentages of viable (FIG. 14A), apoptotic (FIG. 14B) and necrotic SCC13 cells (FIG. 14C) as well as viable (FIG. 14D), apoptotic (FIG. 14E) and necrotic A431 cells (FIG. 14F) were determined by FCM-analysis with Annexin V-FITC and Propidium iodide. Values are expressed as mean value±SD of 6 independent experiments. Asterisk symbols indicate differences between controls. The significance levels are graphically shown as follows: *$p \leq 0.001$, $p \leq 0.01$, *$p \leq 0.05$, ns $p \leq 0.05$ (one-way ANOVA followed by Tukey's post-hoc test).

Compared to the respective negative controls, both cell lines showed a significant total reduction of cell viability, being coherent to a significant increase of apoptotic cells in all cell lines (FIG. 14A, 14B, 14D, 14E). In SCC13 cells a significant reduction of cell viability was observed at every dosage, reaching from 84.35% (±1.3%) at lowest dosage of 200 µmol/l GP-2250 to a cell viability of 52.89% (±2.9%) at a dosage of 400 µmol/l GP-2250 (FIG. 14A).

Figure 14D:
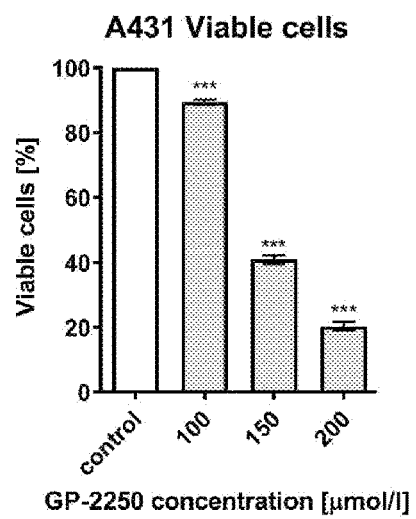
Figure 14B:
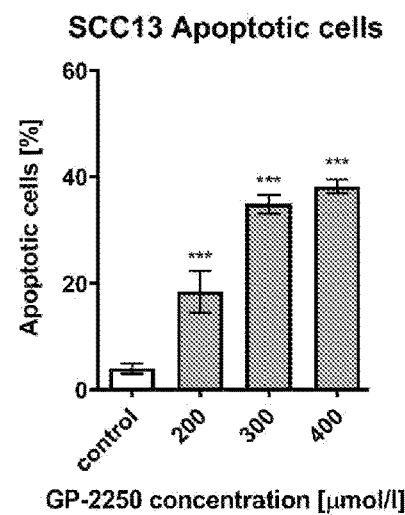
Figure 14E:
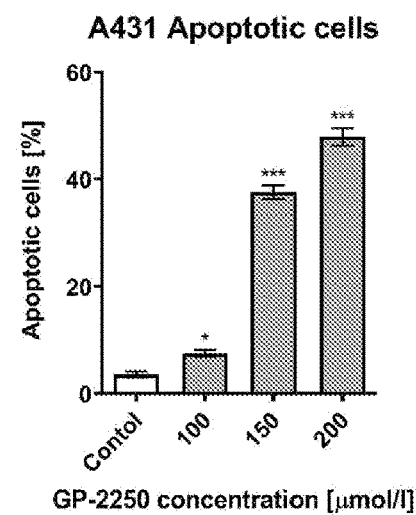
Figure 14C:
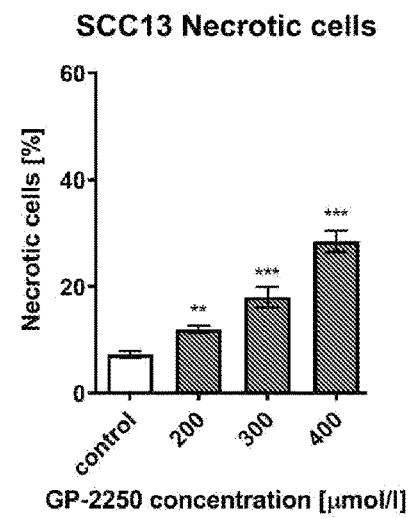
Figure 14F:
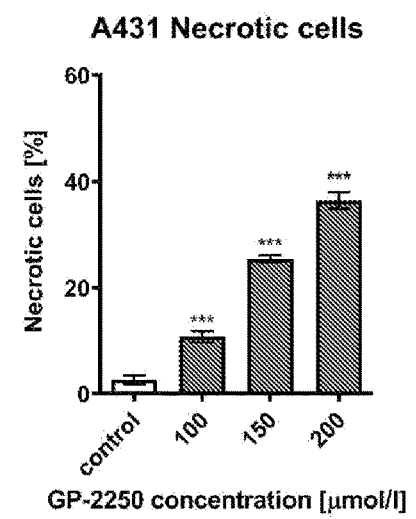

In A431 cells a stronger reduction of cell viability was observed, with at highest dosage of 200 µmol/l GP-2250 a cell viability reduction to 20.35% (±1.2%) (FIG. 14D). Similar significant cell line dependent patterns were observed comparing the apoptotic and necrotic effect of substance GP-2250, showing a greater contribution of apoptosis on cell death than the one of necrosis in both cell lines (FIGS. 14B, 14C, 14E, 14F). In the SCC13 cell line the highest used dosages of GP-2250 lead to 38.15% (±1.3%) apoptotic cells and to 20.45% (±0.5%) of necrotic cells; in A431 cells 47.95% (±1.6%) and 36.46% (±1.6%) respectively (FIGS. 14B, 14C, 14E, 14F).

Example 12

Figure 15A:
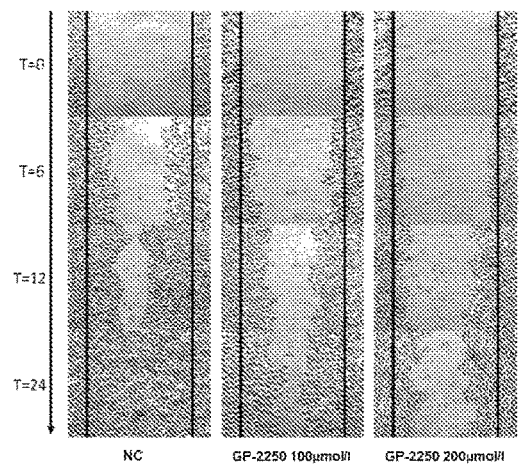
FIGS. 15A-15D show reduction in cutaneous squamous carcinoma cell motility in the cell migration assay.
Figure 15B:
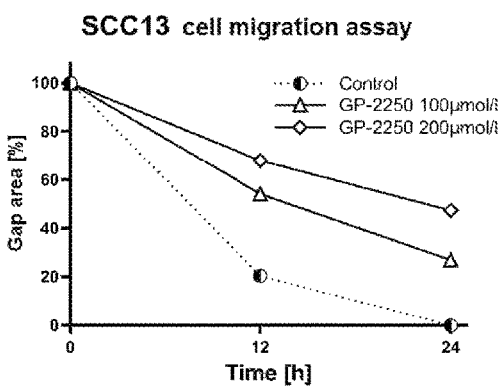
Figure 15C:
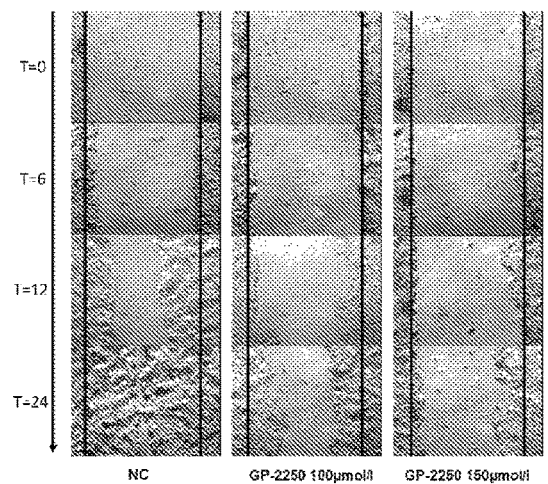
Figure 15D:
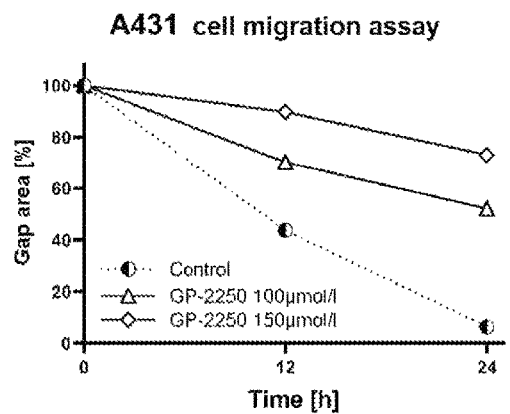

Cell motility of cSCC cells A431 and SCC13 was analyzed using cell migration assays. Cells were seeded in 6-well culture plates to a density of 6×10⁵ and grown to 100% confluence in approximately 24 hours, depending on the cell line. An artificial gap of approximately 1100 μm wide was then generated using a p200 pipet tip and cells were incubated separately with substance GP-2250 and ddH2O for negative control. Duplicate testing was performed for all concentrations. For each cell line the two closest concentrations to the IC$_{50}$ (half maximal inhibitory concentration) were chosen: 100 and 200 μmol/l GP-2250 for cell line A431 and 100 and 150 μmol/l for the SCC13 cell line. Cells at the gap edge polarized and migrated into the gap space. The cell migration (gap closure) was recorded using differential interference contrast (DIC) microscopy in order to not only observe and measure the cell progression, but also to visualize the change in shape, size and behavior of the incubated cells. Pictures were taken at 0, 6, 12 and 24 hours as shown in FIGS. 15A and 15C.

Cell migration assays were conducted with SCC13 and A431 cell lines in order to analyze and visualize the effects of substance GP-2250 on cell migration. Both cell lines were separately incubated with 100 and 150 μmol/l GP-2250 for the SCC13 cell line and 100 and 200 μmol/l respectively for the A431 cell line. Duplicate testing was performed for all chosen concentrations. Cell migration was recorded using DIC microscopy.

Compared to untreated controls, rising concentrations of GP-2250 lead to significant increasing anti-migratory effects (FIG. 15A-15D). While the gaps of the control groups measured after 24 hours 0.07% (±0.3%) in the SCC13 cells and in 6.36% (±0.3) in A431 cells, percentages of gap closure were significantly higher with applied GP-2250 in both cell lines leading to 47.26% (±0.8%) gap closure at highest dosages in SCC13 cells and 73.03% (±1.0%) in A431 cells respectively.

Morphological changes in shape and size were observed after 24 hours of incubation with substance GP-2250. Both cSCC cell lines exhibited on one hand cytoplasmic shrinkage and vacuolization and on the other hand cytoplasmic swelling. Cells either detached from each other or floated in the medium. These findings suggest substance induced apoptosis and respectively necrosis.

Any of the above protocols or similar variants thereof can be described in various documentation associated with a pharmaceutical product. This documentation can include, without limitation, protocols, statistical analysis plans, investigator brochures, clinical guidelines, medication guides, risk evaluation and mediation programs, prescribing information and other documentation that may be associated with a pharmaceutical product. It is specifically contemplated that such documentation may be physically packaged with an pharmaceutical product according to the present disclosure as a kit, as may be beneficial or as set forth by regulatory authorities.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. A method of reducing or inhibiting cancer cell migration in a subject having a pancreatic cancer, an ovarian cancer, or a squamous cell carcinoma comprising administering an effective amount of a compound of formula I

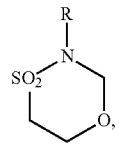

Formula I wherein R is H, an alkyl, or benzyl, to the subject.

2. The method of claim 1, wherein the compound is administered orally, intravenously, topically, or a combination thereof.

3. The method of claim 1, wherein the compound is

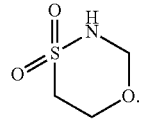

2250

4. The method of claim 1, comprising administering 0.1 g to about 100 g of the compound per day.

5. The method of claim 1, comprising administering 5 g to about 30 g of the compound per day.

6. The method of claim 1, comprising administering the compound in a gel, capsule, tablet, or solution.

7. The method of claim 1, comprising administering the compound in a pharmaceutical composition at a concentration of about 0.01 to about 3 % w/v.

8. The method of claim 1, comprising administering the compound in a pharmaceutical composition at a concentration of about 0.01 μg/ml to about 1000 μg/ml.

9. The method of claim 1, comprising administering the compound in a pharmaceutical composition containing about 0.01 to about 3% taurolidine and/or taurultam.

10. The method of claim 1, comprising administering the compound orally to the subject.

11. A method of treating a subject having a squamous cell carcinoma, an ovarian cancer, or a pancreatic cancer comprising orally, intravenously, or topically administering 0.1 g to about 100 g of a compound of formula I

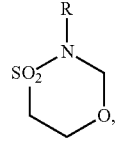

Formula I wherein R is H, an alkyl, or benzyl, to the subject.

12. The method of claim 11, wherein the squamous cell carcinoma is a cutaneous squamous cell carcinoma.

13. The method of claim 11, wherein the compound is administered orally, intravenously, topically, or a combination thereof.

14. The method of claim 11, wherein the compound is

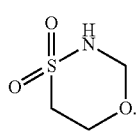

15. The method of claim 11, comprising administering 0.1 g to about 100 g of the compound per day.

16. The method of claim 11, comprising administering 5 g to about 30 g of the compound per day.

17. The method of claim 11, comprising administering the compound in a gel, capsule, tablet, or solution.

18. The method of claim 11, comprising administering the compound in a pharmaceutical composition at a concentration of about 0.01 to about 3% w/v.

19. The method of claim 11, comprising administering the compound in a pharmaceutical composition at a concentration of about 0.01 µg/ml to about 1000 µg/ml.

20. The method of claim 11, comprising administering the compound in a pharmaceutical composition containing about 0.01 to about 3% taurolidine and/or taurultam.

* * * * *